(12) United States Patent
Abdou

(10) Patent No.: US 7,291,152 B2
(45) Date of Patent: Nov. 6, 2007

(54) BONE FIXATION SYSTEM AND METHOD OF IMPLANTATION

(76) Inventor: M. Samy Abdou, 7790 Doug Hill, San Diego, CA (US) 92127

( * ) Notice: Subject to any disclaimer, the term of this patent is extended or adjusted under 35 U.S.C. 154(b) by 160 days.

(21) Appl. No.: 10/825,916

(22) Filed: Apr. 15, 2004

(65) Prior Publication Data
US 2005/0004573 A1    Jan. 6, 2005

Related U.S. Application Data

(60) Provisional application No. 60/463,805, filed on Apr. 18, 2003.

(51) Int. Cl.
*A61B 17/58* (2006.01)
(52) U.S. Cl. ........................................ 606/61
(58) Field of Classification Search ............... 606/61, 606/69–72
See application file for complete search history.

(56) References Cited

U.S. PATENT DOCUMENTS

| | | | |
|---|---|---|---|
| 4,289,123 A | 9/1981 | Dunn | |
| 5,133,717 A | 7/1992 | Chopin | |
| 5,147,360 A | 9/1992 | Dubousset | |
| 5,152,303 A | 10/1992 | Allen | |
| 5,261,911 A | 11/1993 | Carl | |
| 5,380,324 A | 1/1995 | Muller et al. | |
| 5,545,164 A | 8/1996 | Howland | |
| 5,603,714 A | 2/1997 | Kaneda et al. | |
| 5,616,142 A | 4/1997 | Yuan et al. | |
| 5,662,652 A | 9/1997 | Schafer et al. | |
| 5,681,312 A | 10/1997 | Yuan et al. | |
| 5,683,391 A | 11/1997 | Boyd | |
| 5,928,233 A | 7/1999 | Apfelbaum | |
| 5,993,449 A | 11/1999 | Alexander et al. | |
| 6,117,135 A * | 9/2000 | Schlapfer | 606/61 |
| 6,214,005 B1 | 4/2001 | Benzel et al. | |
| 6,306,136 B1 | 10/2001 | Baccelli | |
| 6,524,315 B1 | 2/2003 | Selvitelli et al. | |
| 6,547,790 B2 | 4/2003 | Harkey, III et al. | |
| 6,645,207 B2 * | 11/2003 | Dixon et al. | 606/61 |
| 6,663,631 B2 * | 12/2003 | Kuntz | 606/61 |
| 6,830,571 B2 * | 12/2004 | Lenke et al. | 606/61 |
| 6,884,243 B2 * | 4/2005 | Sellers | 606/71 |
| 2001/0047172 A1 | 11/2001 | Foley et al. | |
| 2002/0055741 A1 | 5/2002 | Schlapher | |
| 2002/0099386 A1 | 7/2002 | Beger et al. | |
| 2002/0183755 A1 | 12/2002 | Michelson | |
| 2003/0078583 A1 | 4/2003 | Biederman et al. | |
| 2004/0133207 A1 | 7/2004 | Abdou | |
| 2004/0204713 A1 | 10/2004 | Abdou | |
| 2005/0177163 A1 | 8/2005 | Abdou | |

FOREIGN PATENT DOCUMENTS

| | | |
|---|---|---|
| WO | 04/032726 | 4/2004 |
| WO | 04/062482 | 7/2004 |
| WO | 04/093702 | 11/2004 |

* cited by examiner

*Primary Examiner*—Eduardo C. Robert
*Assistant Examiner*—Michael J. Araj
(74) *Attorney, Agent, or Firm*—Fish & Richardson P.C.; Fred C. Hernandez

(57) ABSTRACT

Disclosed is a bone fixation device for retaining vertebra of a spinal column in a desired spatial relationship. In one embodiment, the device comprises a first member connectable to a first vertebra and a second member connectable to a second vertebra and interconnected with the first member. The first and second members are movable relative to one another across a range of motion. An adjustor member transitions between a first state and a second state, wherein the range of motion between the first member and second member spans a first distance when the adjustor member is in the first state, and wherein the range of motion between the first member and second member spans a second distance when the adjustor member is in the second state.

11 Claims, 21 Drawing Sheets

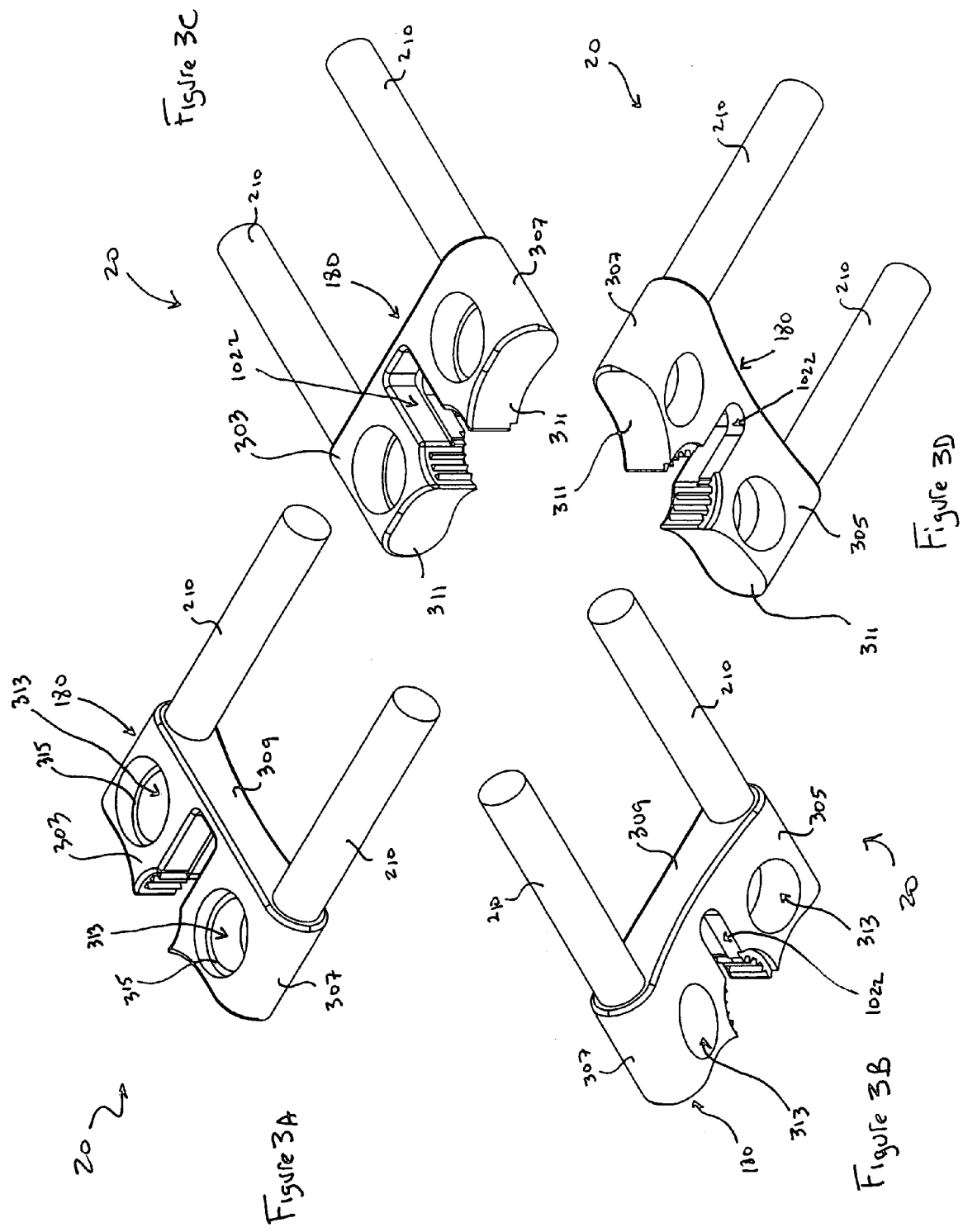

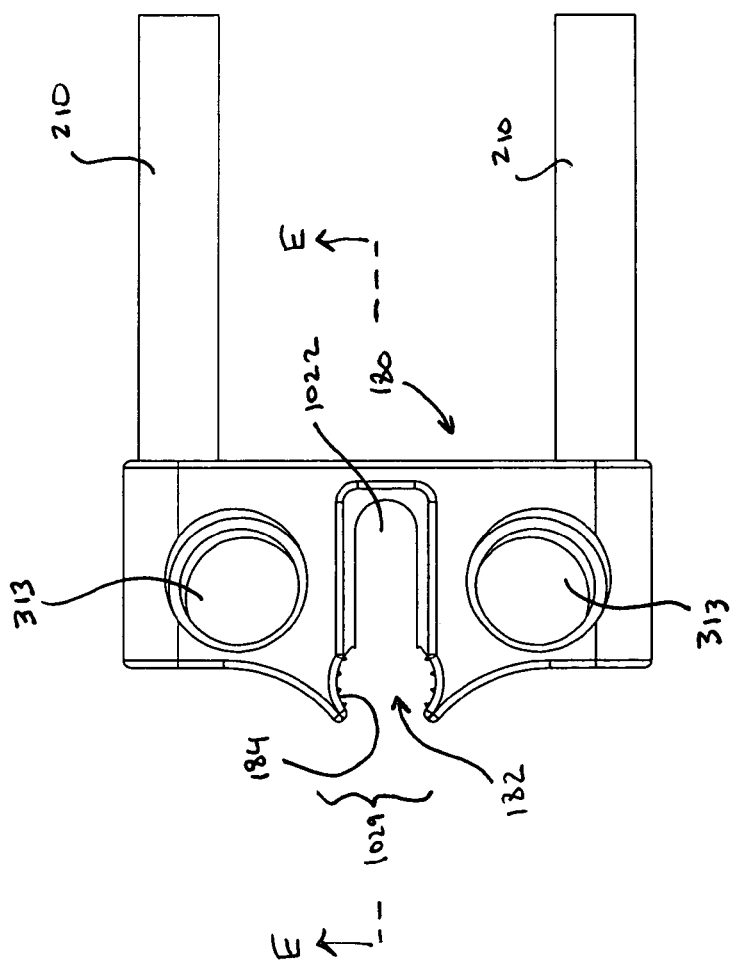
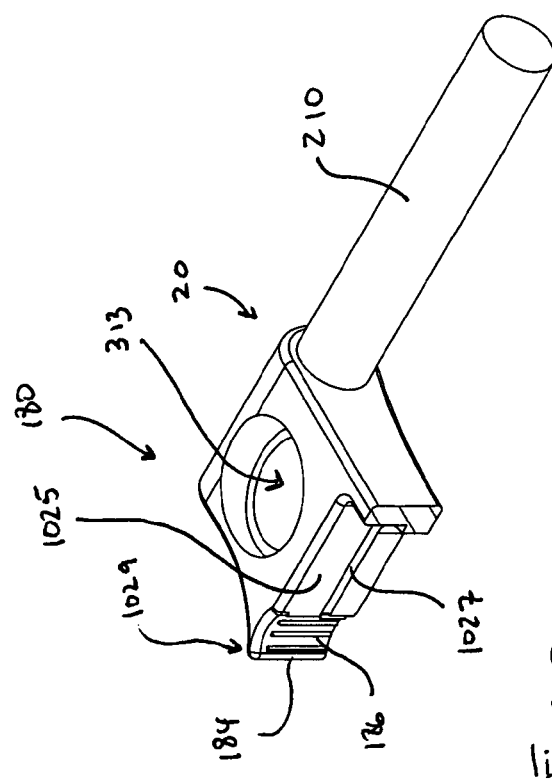

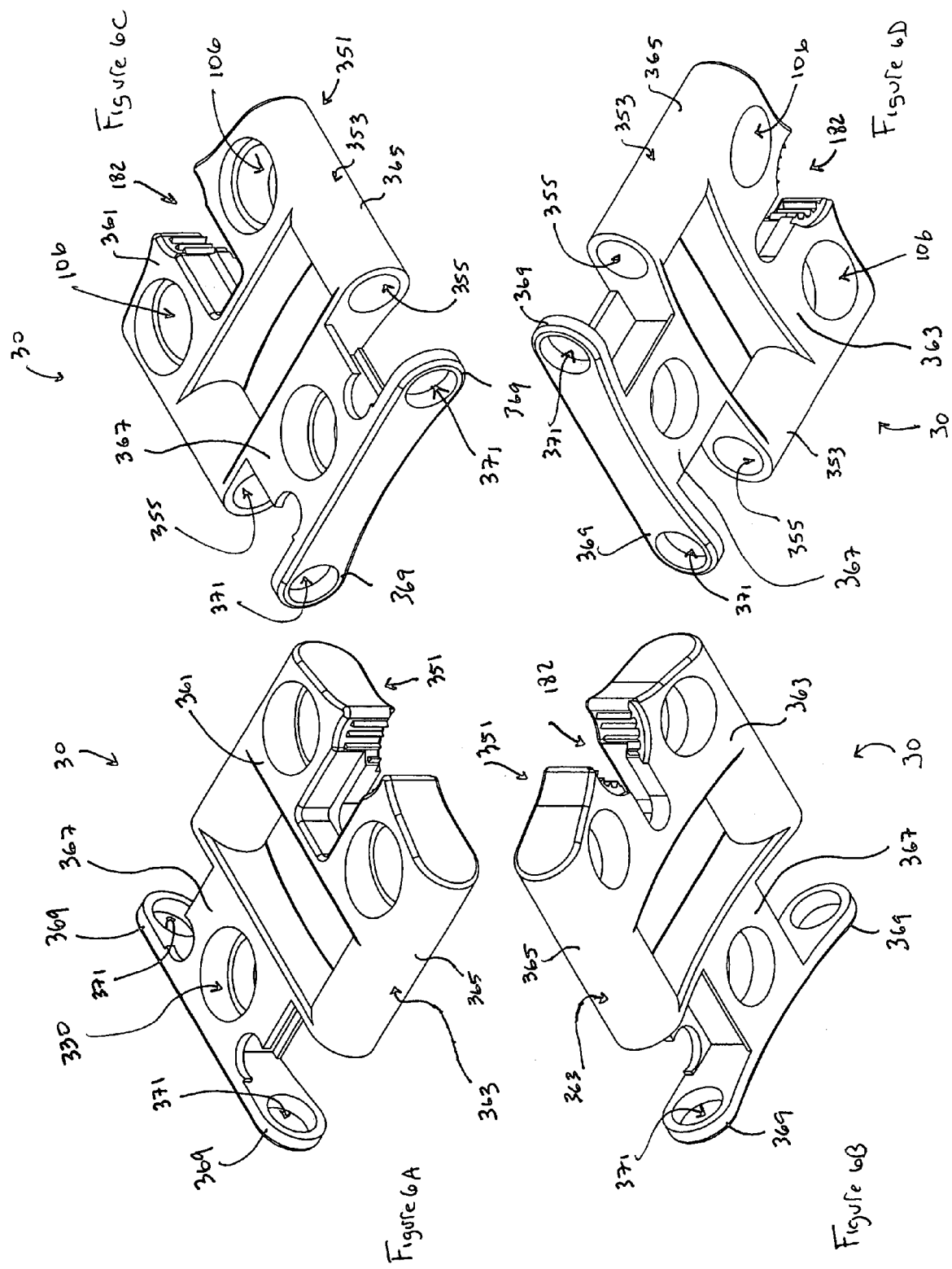

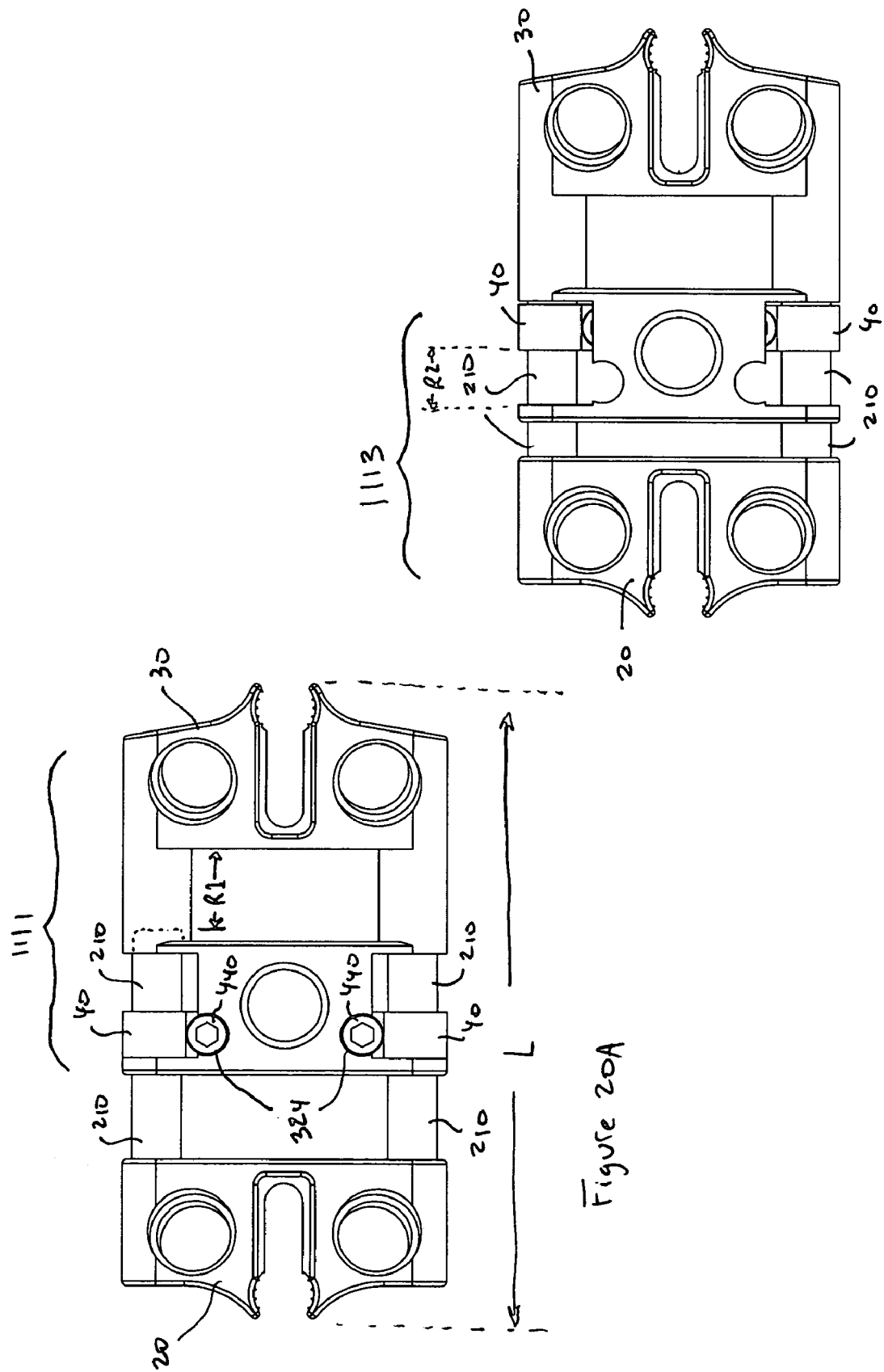

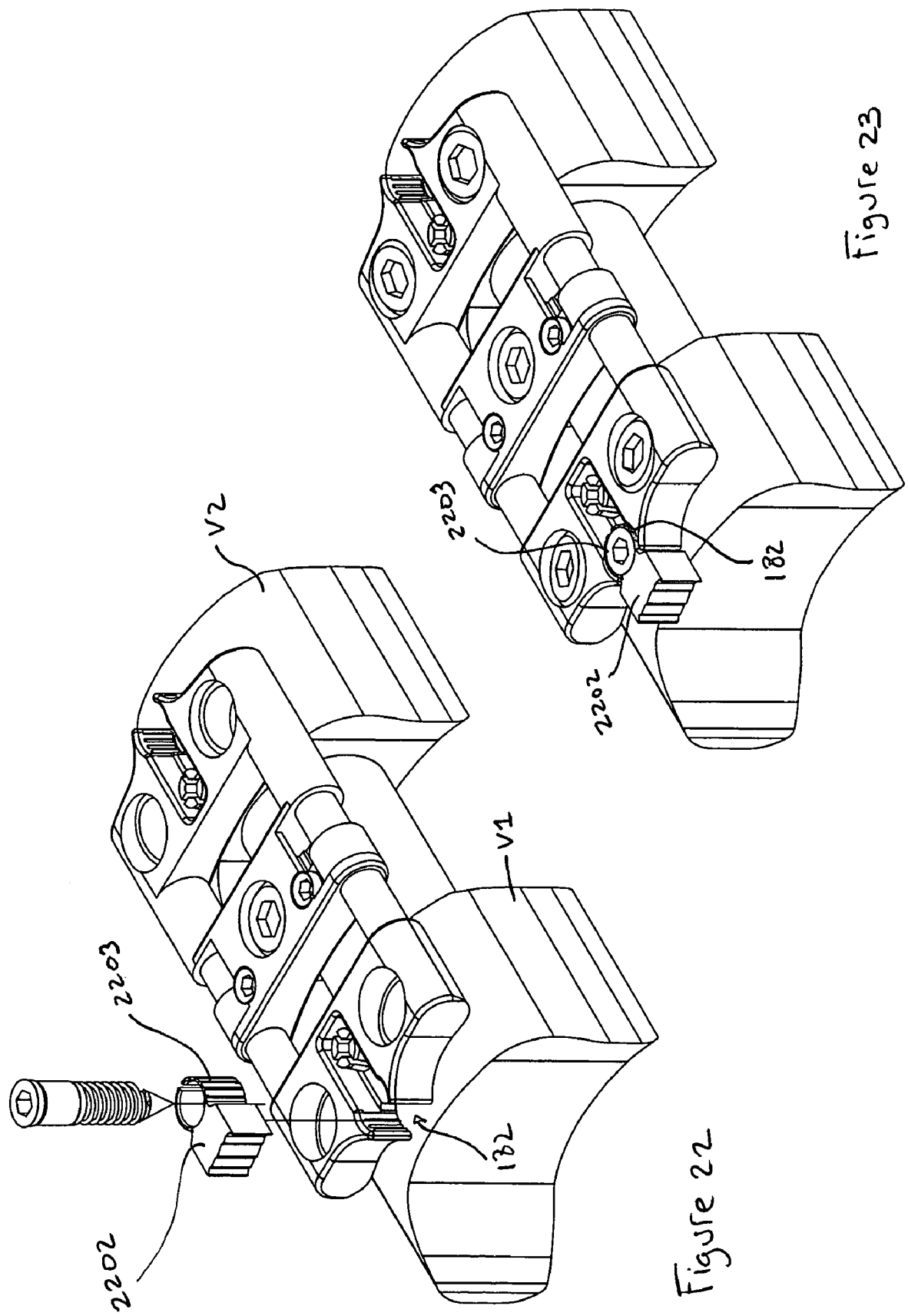

BONE FIXATION SYSTEM AND METHOD OF IMPLANTATION

CROSS-REFERENCES TO RELATED APPLICATIONS

This application claims priority to now abandoned U.S. Provisional patent application No. 60/463,805 filed on Apr. 18, 2003. Priority of the aforementioned filing date is hereby claimed, and the disclosure of the Provisional Patent Application is hereby incorporated by reference in its entirety.

BACKGROUND

This disclosure is directed at skeletal bone fixation systems, and more particularly to a fixation device and method for retaining vertebrae of a spinal column in a fixed spatial relationship.

Bone fixation systems are used to adjust, align and maintain the spatial relationship(s) of adjacent bones or bony fragments after surgical reconstruction of skeletal segments. Such systems may be comprised of bone distraction devices, skeletal bone fixation devices, bone screws and/or bone cables, and any additional instruments needed for implant placement.

Whether for degenerative disease, traumatic disruption, infection or neoplastic invasion, surgical reconstructions of the bony skeleton are common procedures in current medical practice. Regardless of anatomical region or the specifics of the reconstructive procedure, many surgeons employ an implantable skeletal fixation device to adjust, align and maintain the spatial relationship(s) of adjacent bones or bony fragments during postoperative healing. These devices are generally attached to the bony elements using bone screws or similar fasteners and act to share the load and support the bone as osteosynthesis progresses.

Available systems used to fixate the cervical spine possess several shortcomings in both design and implantation protocols. These devices are manufactured and provided to the surgeon in a range of sizes that vary by a fixed amount. This mandates that a large number of different sizes must be made and inventoried—adding to cost for manufacturer, vendor, and end user (hospitals). More importantly, the pre-manufactured devices may not precisely fit all patients forcing surgeons to choose between a size too small or too large.

Current cervical systems are not modular, and will not permit addition of one fixation device to another for extension of the bony fusion at a future date. It is accepted that fusion of a specific spinal level will increase the load on, and the rate of degeneration of, the spinal segments immediately above and below the fused level. As the number of spinal fusion operations have increased, so have the number of patients who require extension of their fusion to adjacent levels. Currently, the fixation device must be removed from the spine and replaced with a longer device in order to extend the fusion to adjacent levels. This surgical procedure necessitates re-dissection through the prior, scarred operative field and substantially increases the operative risk to the patient. Further, since mis-alignment of the original device along the vertical axis of the spine is common, proper implantation of the replacement often requires that the new bone screws be placed in different bone holes. The empty holes that result may act as stress concentration points within the vertebral bodies, as would any empty opening or crack within a rigid structural member, and lead to bone fracture and subsequent device migration.

Current systems may provide fixation that is too rigid. Since bone re-absorption at the bone/graft interface is the first phase of bone healing, fixation that is too rigid will not permit the bone fragments to settle and re-establish adequate contact after initial bone absorption. This process will lead to separation of the bony fragments and significantly reduce the likelihood of bony fusion. Unsuccessful bone fusion may lead to construct failure and will frequently necessitate surgical revision with a second operative procedure.

Benzel (U.S. Pat. No. 5,681,312) and Foley (patent application Pub. No. US2001/0047172A1) have independently proposed bone fixation systems designed to accommodate bone settling. In either system, however, bony subsidence causes one end of the device to migrate towards an adjacent, normal disc space. This is highly undesirable since, with progressive subsidence, the device may overly the disc space immediately above or below the fused segments and un-necessarily limit movement across a normal disc space. Clearly, accommodation of bone settling at the end of the fixation system is a sub-optimal solution.

The implantation procedures of current fixation systems have additional shortcomings. Distraction screws are used during disc removal and subsequent bone work and these screws are removed prior to bone plate placement. As is known to those skilled in the art, the distraction screws are mounted into the bone and used to separate the bones and provide access to the space therebetween. After the distraction screws are removed, the resulting empty bone holes created by removal of the distraction screws can interfere with proper placement of the bone screws used to anchor the device and predispose to poor alignment along the long axis of the spine. This is especially problematic since the surgical steps that precede device placement will distort the anatomical landmarks required to ensure its proper alignment, leaving the surgeon with little guidance during implantation. For these reasons, bone fixation devices are frequently placed "crooked" in the vertical plane and often lead to improper bony alignment.

The empty bone holes left by the removal of the distraction screws also act as stress concentration points within the vertebral bodies, as would any empty opening or crack within a rigid structural member, and predispose them to bone fracture and subsequent device migration. Improper fixation device placement and bony fractures can significantly increase the likelihood of construct failure and lead to severe chronic pain, neurological injury, and the need for surgical revision with a second procedure.

While many vertebral fixation systems use bone plates, some systems employ longitudinal rods to connect and fixate the vertebra bodies. A number of these devices have been illustrated in U.S. Pat. No. 5,147,360, 5,152,303, 5,261,911, 5,380,324, 5,603,714, 5,662,652, 5,683,391 and 6,214,005. They share the shortcomings enumerated above and exhibit additional limitations of their own. Rod-based systems are usually larger and more bulky than plate-based systems, making these devices difficult to apply in regions with limited space such as the anterior aspect of the cervical spine. Further, these devices often require the assembly of multiple segments before implantation and are notoriously cumbersome to use. For those reasons, many surgeons will limit their use of rod-based fixation devices in general and avoid them altogether in regions with limited space, such as the anterior aspect of the cervical spine.

In view of the proceeding, it would be desirable to design an improved rod fixation system and placement protocol. The new device desirably provides the reliable bone fixation characteristic of rod-based systems as well as address the shortcomings enumerated above. The device is desirably of variable length and able to accommodate any length within a pre-defined range. It is desirably capable of accommodating bone settling at the level of bony subsidence and not encroach upon normal, adjacent disc spaces. The device desirably readily permits extension of the fusion at a future without requiring device removal. And, unlike prior art, the device desirably requires no intra-operative assembly, provides ease of use and is sufficiently compact so as permit application within the anterior aspect of the cervical spine.

SUMMARY

Disclosed is a modular distraction screw and a rod-based bone fixation system. The distraction screw is placed as the first step of surgery when all relevant landmarks are still intact and used for the bone work prior to device placement. After completion of the bone work, a proximal end of the distraction screw is detached, leaving one or more distal segments still implanted in the upper-most and lower-most vertebral bodies. The distal segments are used to guide the bone fixation device into the correct placement position and serve to hold it stationary while the bone screws are placed. Since the distraction screws were placed with intact surgical landmarks, use of the distal segments to guide the device significantly increases the likelihood of its proper placement. In addition, this placement method leaves no empty bone holes to serve as stress concentration points and further weaken the vertebral bodies.

In one embodiment, the bone fixation device includes two sliding components, with one component rigidly affixed onto the vertebral body above the fused space and the other affixed onto the vertebra below. The rod-based sliding segment of each sliding component permits movement along the longitudinal axis of the spine but limits movement in all other planes. A third component comprised of an adjustor component is used to control the range of motion between the first and second sliding components. The relationship between the third, adjustor component and one of the sliding components will determine the extent of variation permitted in the fixation device's overall length. The third component can be locked or unlocked to control the range of motion. When the third component is locked, movement between it and the second sliding component determines the extent of bony subsidence permitted. These design features collectively allow development of a variable length rod-based fixation device that is capable of accommodating bony subsidence at the level of the settling bone, and not at the end of the device.

A modular coupler is placed at either end of the device, permitting extension of the fusion at a later date without device removal. The extension is started by connecting a modified distraction screw to the coupler at the end of the device immediately adjacent to the disc to be removed. A modular distraction screw is inserted into the vertebral body on the other side of the diseased disc space. Alternately, a conventional, one-piece distraction screw (rather than the modular distraction screw described herein) can be used to distract the vertebra during discectomy. The distraction screws are then used to distract and open the intervening disc space. A discectomy and subsequent fusion are performed within that disc space. After completion of the bone work, the modified distraction screw is removed leaving the bare coupler on the end of the fixation device. The proximal segment of the distraction screw is also removed leaving the distal segment attached to the adjacent vertebral body. An extension device is used to span the space between the distal segment of the distraction screw on the adjacent vertebra and the end-coupler on the original device. In this way, the fusion is extended and the newly fused segment is fixated without removal of the original fixation device. Further, the end-coupler can used to correct any improper ("crooked") placement of the original plate by rotating the extension piece into the true vertical.

The rod-based bone fixation system described herein provides ease of use, reliable bone fixation, modular design, accommodation of bone settling, and the ability to interact with an implantable distraction screw. These designs maximize the likelihood of proper device placement, avoid maneuvers that weaken the vertebral bodies, address all shortcomings enumerated above, and provide a substantial advantage over the current and prior art.

In one aspect, there is disclosed is a bone fixation device for retaining vertebra of a spinal column in a desired spatial relationship, comprising: a first member connectable to a first vertebra; a second member connectable to a second vertebra and interconnected with the first member, wherein the first and second members are movable relative to one another across a range of motion; and an adjustor member that transitions between a first state and a second state, wherein the range of motion between the first member and second member spans a first distance when the adjustor member is in the first state, and wherein the range of motion between the first member and second member spans a second distance when the adjustor member is in the second state.

In another aspect, there is disclosed a bone fixation device for retaining vertebra of a spinal column in a desired spatial relationship, comprising: a first member connectable to a first vertebra; a second member connectable to a second vertebra and interconnected with the first member, the first and second members being movable relative to one another; and an adjustor member that can be adjusted to vary the degree of movement of the first member relative to the second member, wherein the degree of movement spans a first range when the adjustor member is in an first state and wherein the degree of movement spans a second range when the adjustor member is in a second state.

In another aspect, there is disclosed a bone fixation device for retaining vertebra of a spinal column in a desired spatial relationship, comprising: a first member connectable to a first vertebra; a second member connectable to a second vertebra and interconnected with the first member, the first and second members being movable relative to one another; and means for adjusting the range of motion of the first member relative to the second member, wherein the range of motion spans a first distance or a second distance.

In another aspect, there is disclosed a bone fixation device for retaining vertebra of a spinal column in a desired spatial relationship, comprising: a first member connectable to a first vertebra; and a second member connectable to a second vertebra and interconnected with the first member, wherein the second member includes a distraction screw coupler that permits the second member or the second vertebra to be coupled to a distraction screw while the second member is connected to the second vertebra.

In another aspect, there is disclosed a bone fixation device for retaining vertebra of a spinal column in a desired spatial relationship, comprising: a first member connectable to a first vertebra; and a second member connectable to a second vertebra and interconnected with the first member, wherein the second member includes an interface configured to be modularly attached to a second bone fixation device.

BRIEF DESCRIPTION OF THE DRAWINGS

FIGS. 3A-3D show various views of a first component of the fixation device

FIG. 4 shows a top view of the first component.

FIG. 5 shows a perspective, cross-sectional view of the first component.

FIGS. 6A-6D show various views of a second component of the fixation device.

FIG. 20A shows a top view of the fixation device with an adjustment component in an unlocked state.

FIG. 20B shows a top view of the fixation device with an adjustment component in a locked state.

FIG. 22 shows a fixation device prior to being coupled to a modular device.

FIG. 23 shows a fixation device coupled to a modular device.

DETAILED DESCRIPTION

Disclosed is a modular bone distraction screw and a rod-based bone fixation device. While they may be used in any skeletal region, these devices are well adapted for use in the spine. Exemplary embodiments of the fixation device, distraction screw and the method of use will be illustrated in this region.

Bone Fixation Device

Figure 1:
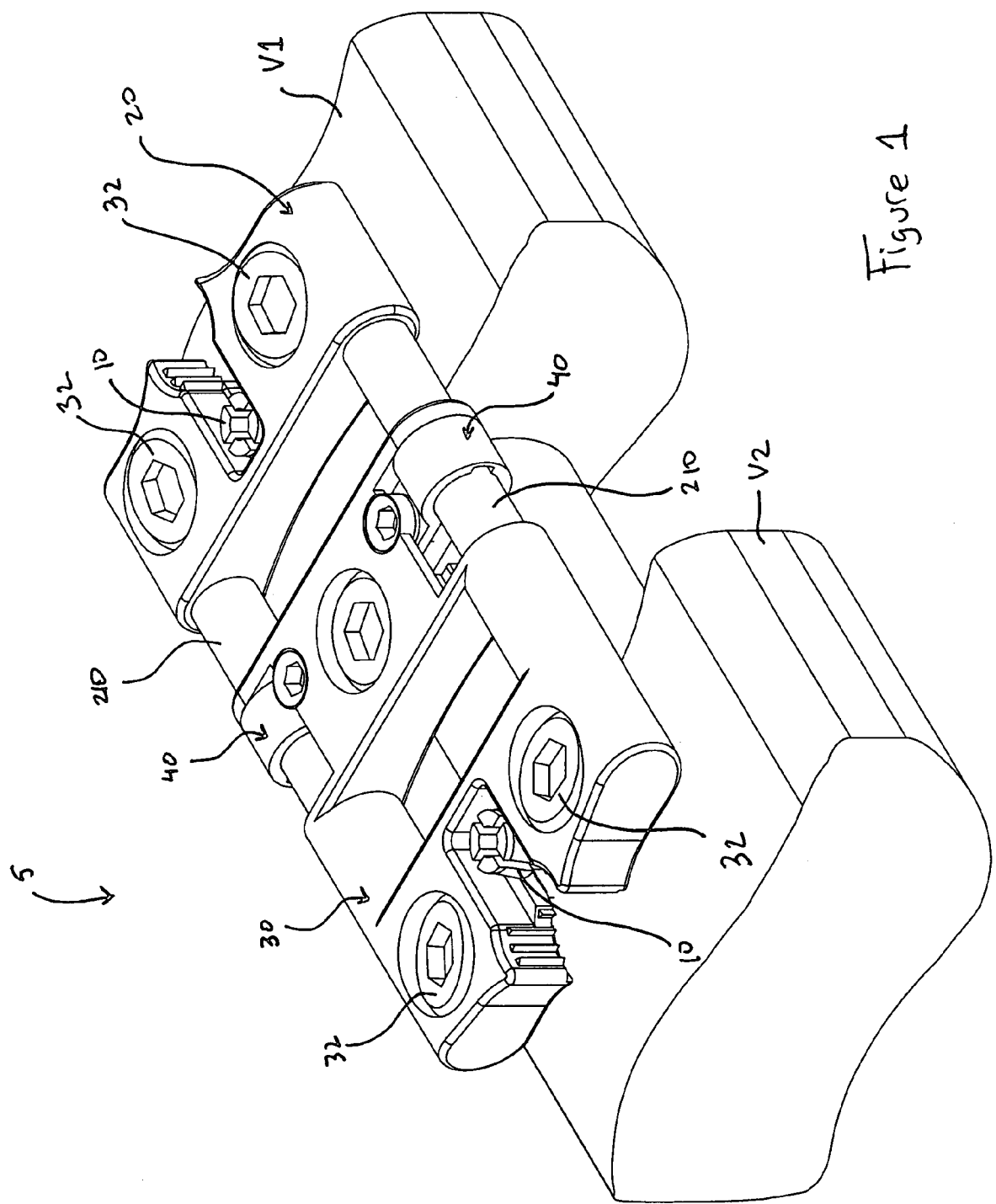
FIG. 1 shows an assembled fixation device immediately prior to attachment to the underlying bone.
Figure 2:
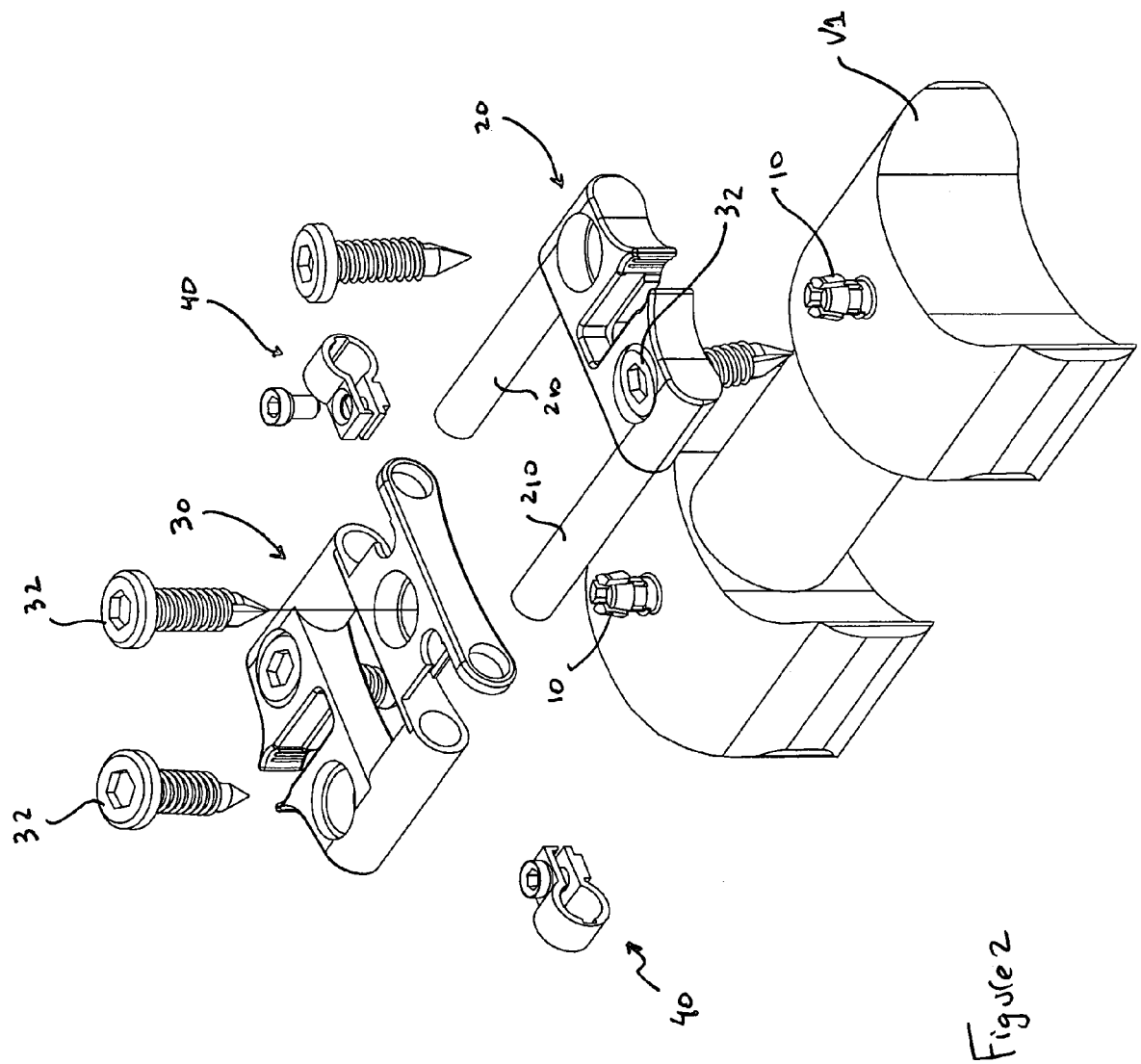
FIG. 2 shows an exploded view of the fixation device.

FIG. 1 is a perspective view of a bone fixation device 5 configured to retain bone portions such as cervical vertebra of a spinal column in a desired spatial relationship. FIG. 1 shows the device 5 in an assembled state and mounted on a spinal column C and interconnecting a first cervical vertebra V1 and a second cervical vertebra V2. FIG. 2 shows the device 5 in an exploded state. For clarity of illustration, the vertebrae are represented schematically and those skilled in the art will appreciate that actual vertebrae include anatomical details not shown in FIG. 1.

With reference to FIGS. 1 and 2, the device 5 includes a first component 20, a second component 30, and one or more adjustor components 40, which are described in more detail below. The first component 20 includes one or more elongate rods 210 that extend along a longitudinal direction. The device 5 further includes a plurality of fasteners, such as bone screws 32, that can be used to fasten the first component 20 and second component 30 to a bone such as the cervical vertebrae V1 and V2. The bone screws 32 may be of any known design that is appropriate for fixation of and implantation into human bone. In addition, the device 5 includes at least one distraction screw 10 for coupling to each of the components 20 and 30, as described in detail below. The bone screws 32 include a head and a shank portion and are used to retain the device 5 against one or more vertebra. The distraction screws 10 are used to distract the vertebra prior to installation of the device 5 and can also be used as a guide for positioning the device 5 on the vertebrae.

The components 20 and 30 are configured to slidingly move relative to one another. In one embodiment, the component 30 slides along elongate rods 210 that extend from the first component 20 such that the component 30 can slide along a span, or degree, of linear movement. Alternately, the rods 210 can have a curvature to provide a curved range of movement. The adjustor component 40 can be manipulated to control the degree of movement that is allowed between the components 20 and 30. As described below, the adjustor component 40 can transition between two or more states that control the range of motion of the first component relative to the second component. When the adjustor component is in an open, or unlocked, state, the first and second components can move across a first range of motion relative to one another. When the adjustor component is in a closed, or locked, state, the first and second components can move across a second range of motion relative to one another. In one embodiment, the "range of motion" comprises linear and sliding movement that spans a predetermined distance. The linear movement can be in the longitudinal direction, which corresponds to the longitudinal axis of the spinal column. In one embodiment, the range of motion is a non-zero value both when the component 40 is in the unlocked or locked state.

Each of the components 20 and 30 of the device 5 includes an interface, such as a borehole, that can receive or that can matingly engage with a distraction screw, as described below. The borehole permits an additional distraction screw to be attached to the underlying vertebra and/or the device 5 without removing the device 5 from the vertebra. The "additional" distraction screw is a distraction screw different from the distraction screw that was originally used in the vertebra.

The device 5 includes a modular aspect that permits the device 5 to be modularly attached to a second device, such as, for example, a coupler to a second bone fixation device, while the device 5 is attached to a spine. The device 5 does not have to be removed from the spine in order to modularly attach the second device to the device 5 in a modular fashion. It should be appreciated that the second device can be a device other than a bone fixation device. When the second device is coupled to a bone fixation device, the modular attachability allows a bone graft to be extended to additional vertebrae without having to remove the original bone fixation device.

Component 20 is now described in more detail with reference to FIGS. 3A-3D and FIGS. 4 and 5. FIGS. 3A-3C shows various perspective view of the component 20. The component 20 includes a main body 180 that is generally rectangular in shape.

At least one rod 210 extends longitudinally from the main body 180.

As best shown in FIGS. 3A and 3C, the main body 180 has an outer surface 303 for facing away from the vertebra V2. As best shown in FIGS. 3B and 3D, the main body 180 also has an inner surface 305 for facing toward the vertebra V1. A pair of side surfaces 307 connect the lateral ends of the outer surface 303 and inner surface 305 to one another. In the illustrated embodiment, the side surfaces 307 are rounded, although it should be appreciated that the side surfaces 307 can also be flat. The main body 180 also has a first end surface 309 (shown in FIGS. 3A and 3B) and rounded, second end surfaces 311 that are interrupted in a central region by a shaft as described further below. It should be appreciated that the main body 180 can have other shapes that are configured for positioning on a cervical vertebra. For example, the inner surfaces 305 can be contoured to conform to the shape of a vertebra on which it will be mounted or the other surfaces can be contoured in a desired manner. Moreover, while not depicted, any component of the device 5 may be further curved in either the vertical or horizontal plane in order to conform to the shape of the bone it is designed to fixate. For example, rod-based bone fixation devices designed to attach onto the anterior aspect of the cervical spine are preferentially convex in both the vertical and horizontal planes.

With reference to FIGS. 3A-3D and FIG. 4, one or more fastener screw shafts 313 extend through the main body of the component 20. Each of the fastener screw shafts 313 is sized to receive a corresponding fastener screw 32 (shown in FIGS. 1 and 2). In one embodiment, a screw head engagement structure, such as an annular lip or shelf 315 (shown in FIG. 3A), is located within each fastener screw shaft 313. The head of a fastener screw can engage the shelf 315 and provide a fastening force thereto during fastening of the component 20 to a vertebra. In the illustrated embodiment, the component 20 has two fastener screw shafts 313, each located near a transverse side of the main body. The fastener screw shafts 313 can be aligned with an axis that is oriented in the true vertical plane, or the axis can form an angle with the vertical. For use in the cervical spine, fastener screw shafts 313 can be angled towards each other in the horizontal plane and away from the rods 210 in the vertical plane. The top opening of the fastener screw shafts 313 may be flush with the outer surface 303 surface, can be curved, or can be further recessed so as to form the shelf 315.

With reference to FIGS. 3A-3D and FIG. 4, an elongate channel 1022 is located in a central region of the main body 180 between the fastener screw shafts 313. FIG. 5 shows a perspective, cross-sectional view of the component 20 along line E-E of FIG. 4 and provides a more detailed view of the structure of the channel 1022. With reference to FIG. 5, the channel 1022 forms a u-shaped side wall 1025 that defines the periphery of the channel 1022. The inferior region of the side walls 1025 of the channel 1022 can be angled with the true vertical so that the top of each channel has a width that is slightly smaller than the width at the bottom of the channel 1022. Channel 1022 serves to mate with and accommodate a screw head of a corresponding distraction screw, such as the screw head 122 of distal segment of the distraction screw 120 described herein. In this regard, a ledge 1027 can be formed on the side wall 1025 to provide a stepped surface that can be engaged by the head of the distraction screw.

It should be appreciated that the shape and configuration of the channel 1022 can be modified into any configuration that is configured to mate with or engage the head of the distraction screw. For example, the channel 1022 can be replaced with a circular hole that is sized to receive a distraction screw.

As mentioned, the second end surfaces 311 of the main body 180 are curved, which forms an outwardly extending projection region 1029 on the end of the main body 180, as shown in FIGS. 4 and 5. The projection 1029 can be located along the midline of the main body 180. The projection forms a modular interface, or an end coupler, comprised of a full thickness borehole 182 with sidewall 184 extends through the main body 180 at the projection region 1029. The end coupler provides the device 5 with the ability to modularly couple to another device. The end coupler has a shape that is configured to modularly mate with a complementary-shaped end coupler on a modular device. For example, one or more engagement structures, are located along the wall 184. The engagement structures, such as the spines 186, are configured to engage a modified distraction screw and/or a modular device (as described below) and can have a variety of shapes or structures configured to accomplish this. In the illustrated embodiment, the engagement structures comprise spines 186. While depicted as triangular, the spines may be projections of any geometric configuration, and may occupy part of or all of the height of wall 184. Further, the spines may extend circumferentially around wall 184 or be limited in number and location along the wall (for example, at the ends). Alternatively, wall 184 may be textured or left smooth. In another embodiment, one or more reliefs or cavities can be located on the wall 184, wherein the reliefs or cavities are sized and positioned to receive a correspondingly-shaped portion of a modular device. The borehole 182 is shown in the Figures as intersecting the channel 1022 such that the borehole 182 opens into the channel 1022. However, it should be appreciated that the borehole 182 may be open onto channel 1022 or may separated from it by an additional wall.

As mentioned, at least one rod 210 extends outwardly and longitudinally from the main body 180 of the component 20. In the embodiment shown in FIGS. 3-5, two rods 210 extend outwardly from opposed, transverse ends of the component 20. The rods 20 intended to mate and interact with component 30. In this regard, the rods 20 are cylindrical and have a circular cross-sectional shape in order to facilitate such mating. However, it should be appreciated that the rods can have other shapes that can mate with the component 30.

The component 30 is now described with reference to FIGS. 6A-6D, which show various perspective views of the component 30. The component 30 includes a main body 351 having a plate like shape. The main body 351 includes a pair of side regions 353 on opposed lateral sides of the component 30. A longitudinally-extending rod shaft 355 (shown in FIGS. 6C and 6D) extends through each of the side regions 353. The rod shafts 355 are sized to receive a corresponding rod 210 of the component 20, as described below. In this regard, each of the rod shafts 355 is positioned so as to be axially aligned with a corresponding rods 210 of the component 20. In one embodiment, the rods 210 are configured to engage with the component 30 in a manner that minimizes the likelihood of the rods 210 disengaging therefrom. In this regard, the end portions of the rods can have diameter that is slightly larger than the entry diameter of the rod shafts 355 so that once the rods 210 are positioned in the rod shafts, the enlarged diameter prevents the rods 210 from inadvertently moving out of the shafts.

With reference to FIGS. 6A-6D, the main body 351 of the component 30 has an outer surface 361 for facing away from the vertebra V2. The main body 351 also has an inner surface 363 for facing toward the vertebra V2. A pair of side surfaces 365 define the periphery of the side regions 353 and connect the lateral ends of the outer surface 361 and inner surface 363 to one another. In the illustrated embodiment, the side surfaces 365 are rounded, although it should be appreciated that the side surfaces 365 can also be flat. It should be appreciated that the main body 351 can have other shapes that are configured for positioning on a cervical vertebra.

A bar 367 extends outwardly from the main body 351 of the component 30, such as along the midline of the component 30. A pair of projections 369 extend laterally outward from lateral ends of the midline bar 367 such that a projection 369 is spaced from and opposed to each of the side regions 353 containing the rod shafts 355. The projections each contain a hole 371 so that each hole 317 is axially aligned with a corresponding rod shaft 355. The holes 371 are sized to receive the rods 210 therethrough.

As in component 20, one or more fastener screw shafts 106 are provided on the main body 351. The central midline bar 367 also has borehole 330 intended to accommodate an additional bone screw 32. As shown in FIG. 1, this screw permits fixation of the device 5 to a bone graft BG. Additionally, an end coupler comprised of a borehole 182 is provided for a distraction screw or for modular connection to another device, as described below. The borehole 182 is equipped with engagement structures, such as spines, as described above with respect to the borehole 182 of component 20.

Figure 7A:
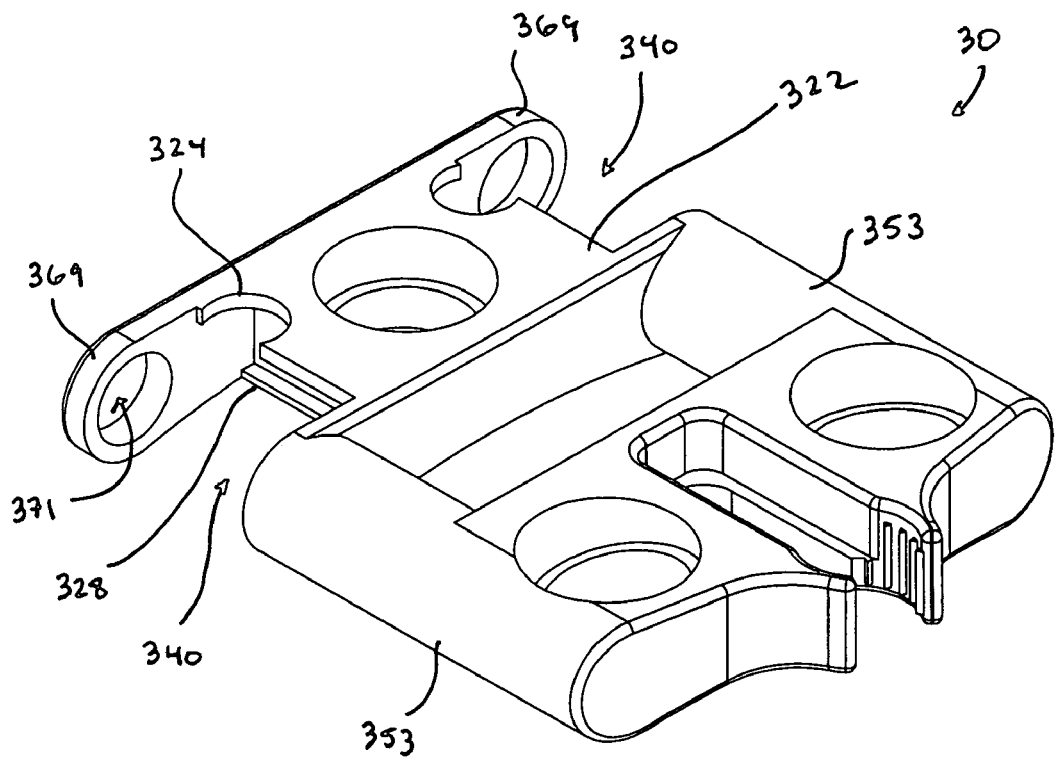
FIGS. 7A and 7B show details of a space in the second component of the fixation device, the space sized to receive a third component.
Figure 7B:
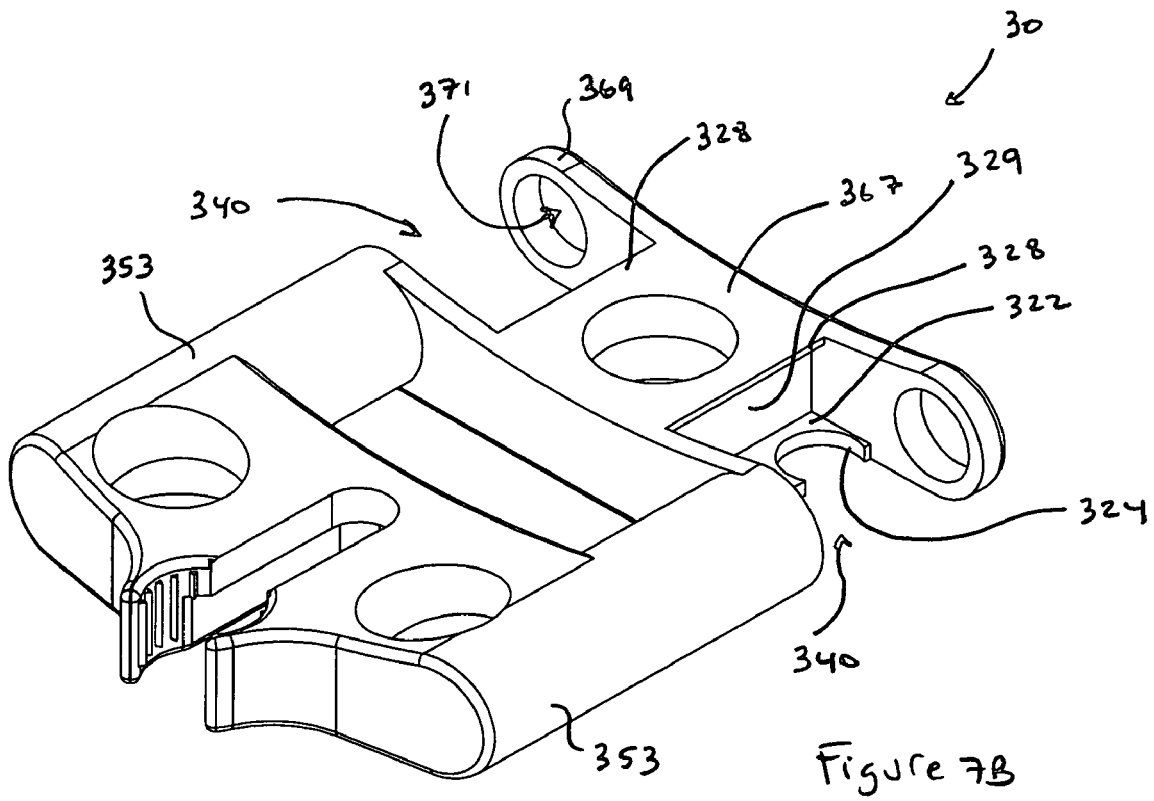

With reference to FIGS. 7A and 7B, a space 340 is formed between each of the projections 369 and the corresponding side region 353. An upper wall 322 extends laterally outward from the bar 367 so as to form a first ledge that overhangs above the space 340 between the projection 369 and the side region 353. A lower wall 328 extends laterally outward from the bar 367 so as to form a second ledge that hangs below the space 340. The upper wall 322 has partial bore 324. Further, upper wall 322 can extend further outward than wall 328 so that the first ledge formed by wall 322 is longer than the second ledge formed by wall 328. Thus, each of the spaces 340 so formed is defined medially by a lateral wall 329 (FIG. 7B), posteriorly by side region 353, anteriorly by projection 369, and is open laterally. As mentioned each projection 369 has a hole 371 so that a corresponding rod 210 can fit through bore hole 371, across space 340 and into rod shaft 355 (FIGS. 6A-6D).

Figure 8B:
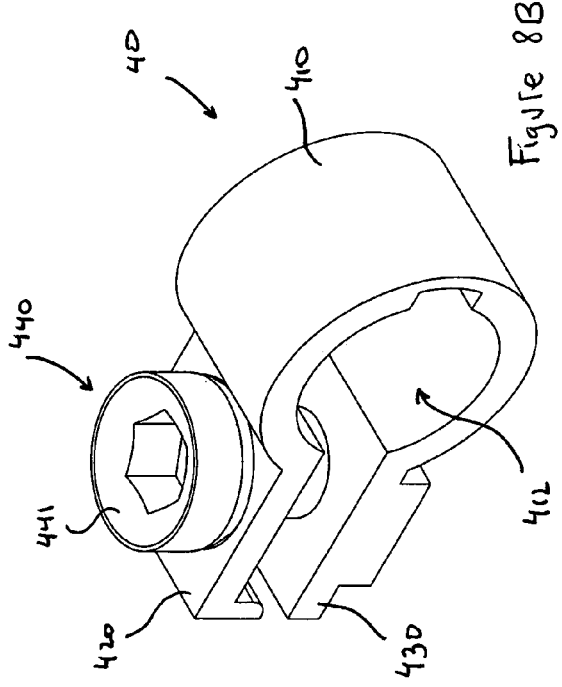
FIGS. 8A and 8B show side and perspective views of an adjustment component of the fixation device in an open state.
Figure 9B:
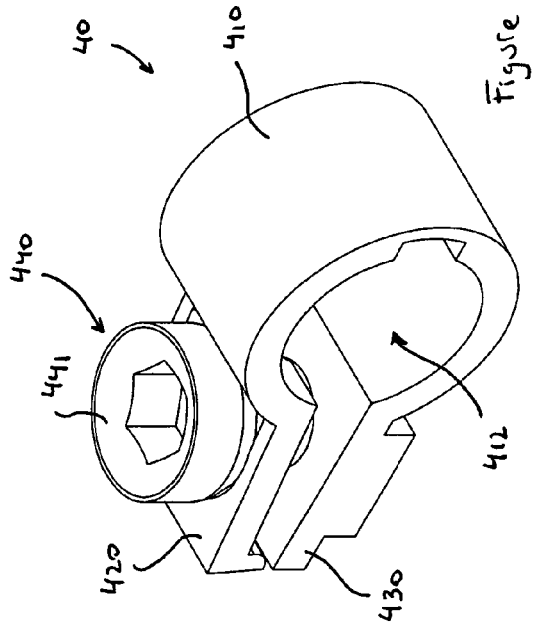
FIGS. 9A and 9B show side and perspective views of an adjustment component of the fixation device in a closed state.
Figure 8A:
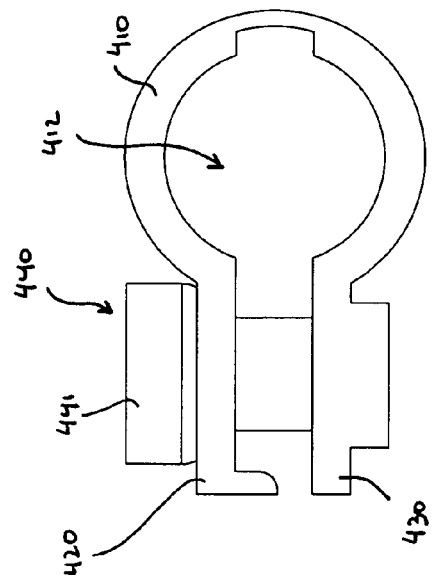
Figure 9A:
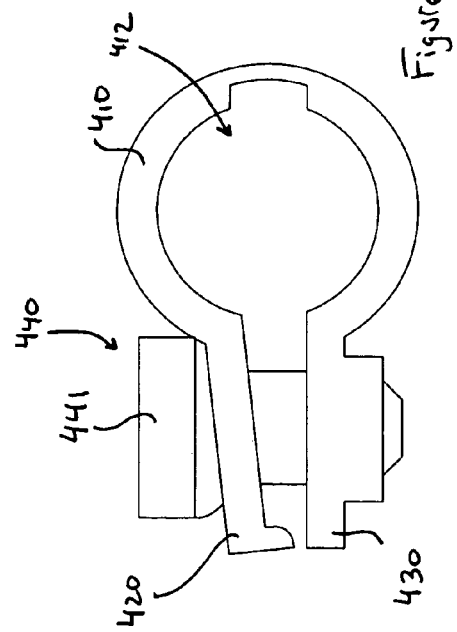

FIGS. 8A and 8b show side and perspective views, respectively, of the component 40 of the device 5. The component 40 is sized to fit into the space 340 (FIGS. 7A and 7B) of component 30. The component 40 is configured to adjustably receive and clasp a corresponding rod 210. In the illustrated embodiment, the component 40 comprises a "C"-shaped collar 410 with bore 412 that is sized to receive therethrough a rod 210. The component 40 also includes side handles 420 and 430 that extend outwardly from the collar 410. A threaded screw 440 with an enlarged head 441 is positionable through bores in handles 420 and 430. In one embodiment, the bore in handle 420 is larger in diameter than the outer diameter of screw 440 and the bore in handle 430 is threaded to engage corresponding threads in the screw 440. The screw 440 can be transitioned between an open state and a closed state. In the closed state, shown in FIGS. 9A and 9B, the screw 440 is tightened into the threads in handle 430 such that the head 441 moves downwardly toward the handle 430, which also causes the handle 420 to move downwardly toward the handle 430 and thereby decrease the size of the bore 412 in the collar 410. In the closed state, the screw 440 is tightened sufficiently such that the 30 collar 410 will grasp and secure the rod 210 therein. In the open state, shown in FIGS. 9A and 9B, the screw 440 is un-tightened sufficiently that the head 441 and the handle 420 move away from the handle 430, causing the bore 412 in collar 410 to widen in size. In the open state, the screw 440 is sufficiently un-tightened such that the rod 210 can slide freely through the bore 412 in the collar 410. Thus, when rod 210 is placed into bore 412, it is freely slideable through the bore 412 while the screw 440 is open. When the screw 440 is closed, the rod 210 is locked or clamped within the collar 410 of component 40.

Figure 10:
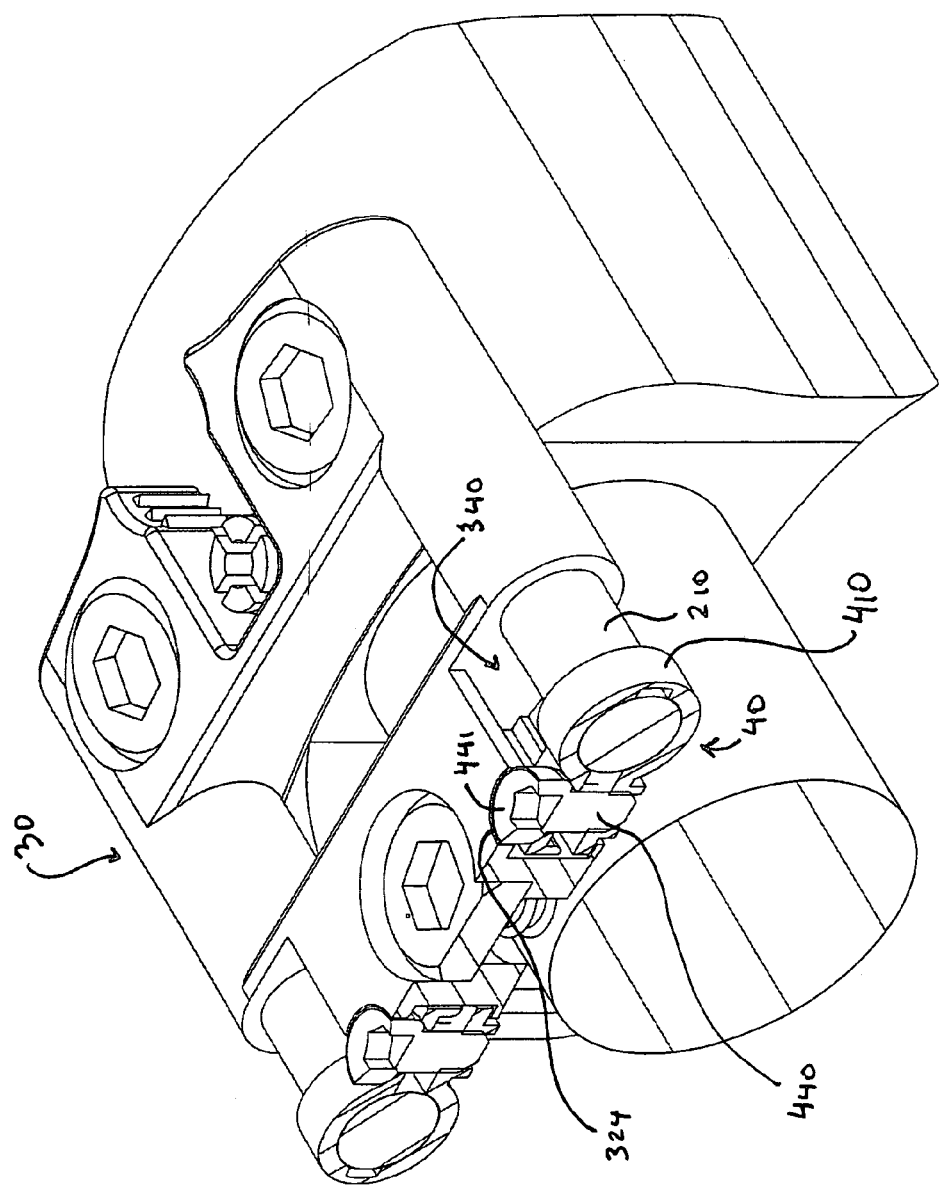
FIG. 10 shows a cross-sectional view of the third component coupled to the second component.

As mentioned, the component 40 is sized to fit within each of the spaces 340 of the component 30. FIG. 10 shows a cross-sectional view of the device 5 with each of two components 40 placed within corresponding spaces 340 of the component 30. FIG. 10 shows the screw 440 in an open state. Note that with screw 440 open, the head 441 of the screw 440 fits in and is positioned within partial bore 324 of the component 30. That is, the screw 440 protrudes outward from the component 40 sufficiently so that it is positioned within and interlocks with the partial bore 324 when the screw 440 is open. With rod 210 extending through component 40 and screw 440 open, the interlocking of the head 441 with the bore 324 prohibits the component 40 from moving within the space 340. However, when the screw 440 is open, the rod 210 (and the attached component 20) can slide through the band 410 unhindered relative to component 30 and 40. Thus, components 30 and 40 act as a unitary piece (by virtue of component 40 interlocking with component 30) and can move relative to component 20 across a predetermined distance in the longitudinal direction with the screw 440 open. This is described in more detail below.

Figure 11:
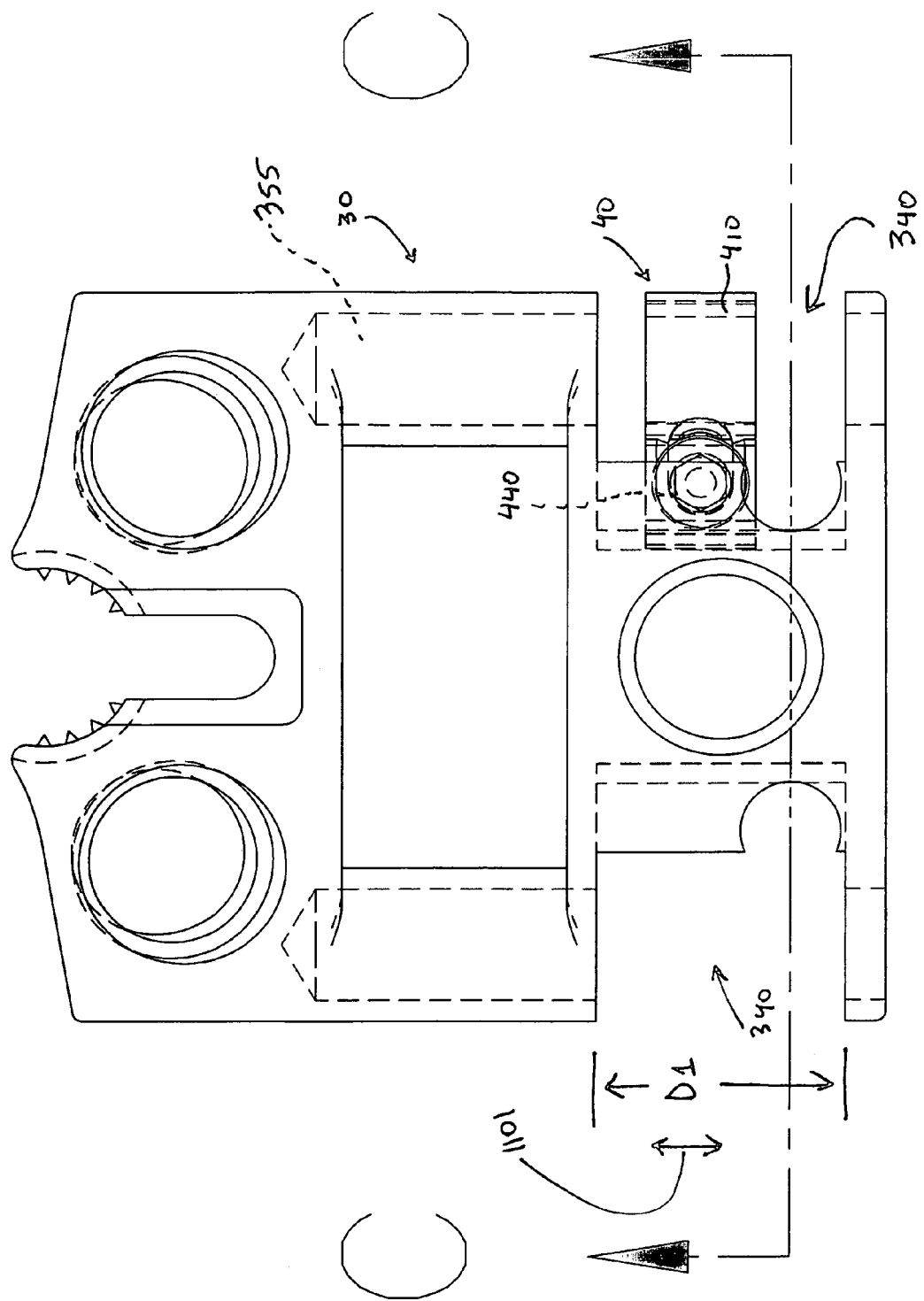
FIG. 11 shows a top view of the third component coupled to the second component.
Figure 12B:
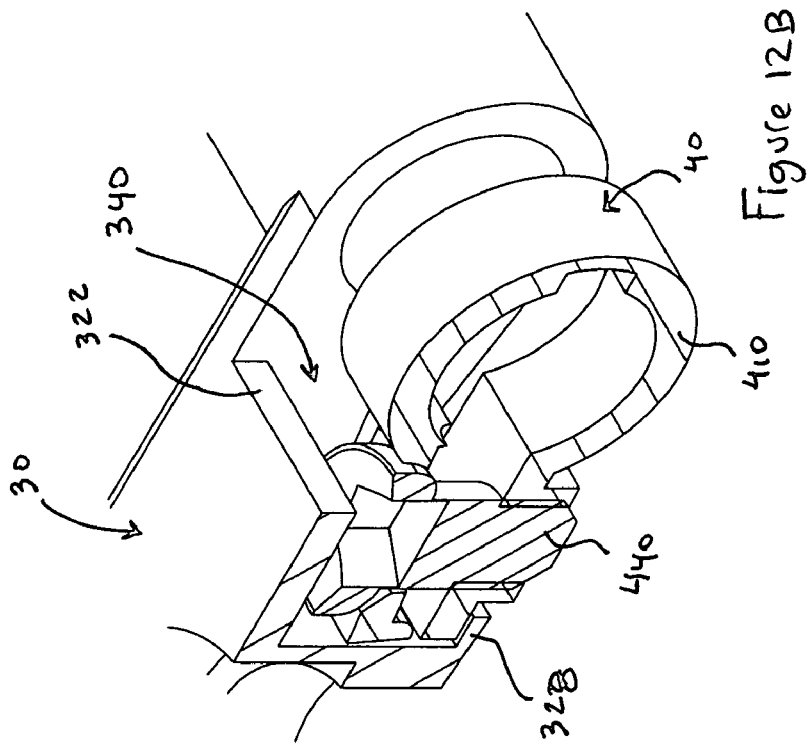
FIG. 12B shows a perspective, cross-sectional view of the third component coupled to the second component along line C-C of FIG. 11.
Figure 12A:
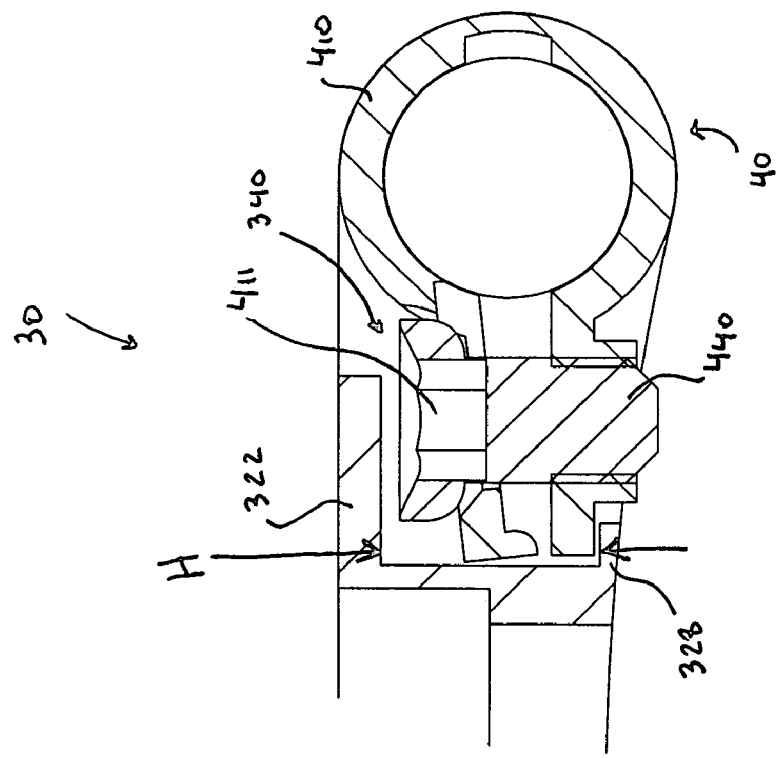
FIG. 12A shows a cross-sectional view of the third component coupled to the second component along line C-C of FIG. 11.
Figure 13:
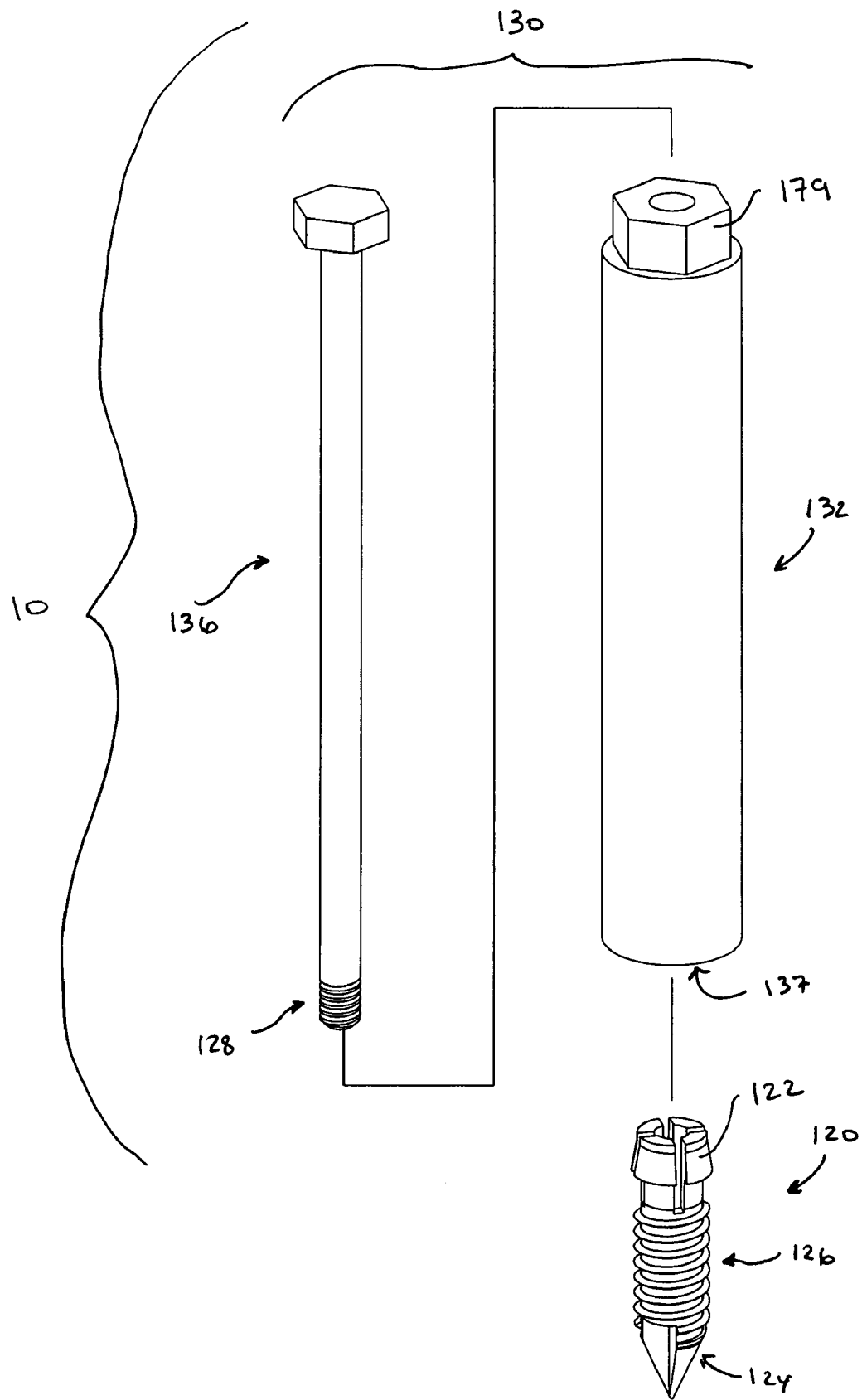
FIG. 13 shows an exploded view of the components of a distraction screw.

FIGS. 11, 12 and 13 show the component 40 located in the space 340 of the component 30 and the screw 440 in a closed state. As shown in the top view of FIG. 11, the component 40 is free to slide across a range of distance D1 within the space 340. The distance D1 is at least partially defined by the longitudinal dimension of the space 340. FIGS. 12A and 12B show cross-sectional views of the components 430 and 40 with the component 40 located in the space 340 and the screw 440 closed. When the screw is closed, at least a portion of the component 40 has a height that is less than the height H of the space 340, which is defined by the upper wall 322 and the lower wall. This permits the component 40 to slidingly move within the space 340 along the longitudinal direction (represented by the arrow 1101 in FIG. 11). As described in more detail below, when the rod 210 is placed through the collar 410 and the screw 440 is closed, the collar 410 closes sufficient to fixedly clasp the rod 210. Thus, with the screw 440 closed, the component 40 is locked to rod 210 of component 20 and both components 20 and 40 can move as a unitary piece relative to component 30 within the space 340 along the direction 1101 (FIG. 11). In this way, the fully assembled device with components 20, 30 and 40 permits a certain amount of movement with screw 440 open and a more limited amount of movement with screw 440 closed, as described more fully below.

Any component of the device can be made of any biologically adaptable or compatible materials. Materials considered acceptable for biological implantation are well known and include, but are not limited to, stainless steel, titanium, tantalum, other metals, combination alloys, various plastics, resins, ceramics, biologically absorbable materials and the like. It would be understood by one of ordinary skill in the art that any system component can be made of any materials acceptable for biological implantation and capable of withstanding the torque required for insertion and the load encountered during use. Any components may be further coated/made with osteo-conductive (such as deminerized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any instrument or device used in implant placement may be made from any non-toxic material capable of withstanding the load encountered during use. Materials used in these instruments need not be limited to those acceptable for implantation, since these devices function to deliver the implantable segments but are not, in themselves, implanted.

Distraction Screws

Figure 14B:
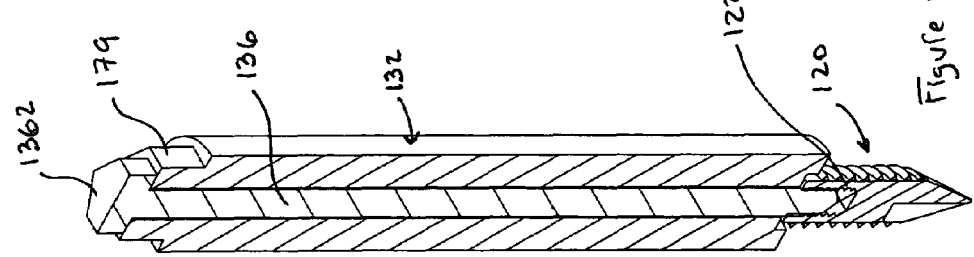
FIGS. 14A and 14B show cross-sectional views of an assembled distraction screw.
Figure 14A:
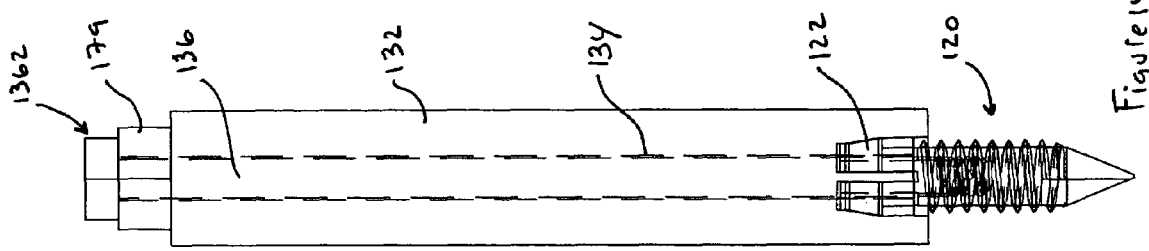

FIG. 13 shows an exploded view of the components of a modular distraction screw 10, which is comprised of a distal segment 120 and a removable proximal 130 segment. The proximal segment includes two pieces, as described below. The distal segment 120 has a head portion 122 and a threaded shank portion 124, which can be securely fastened into bone. The proximal segment 130 is comprised of an elongated body 132 and a deployable member 136 comprised of an elongated rod with a proximal head 1362 and threads 128 on a distal end. The elongated body 132 has a smooth-walled internal bore 134 (FIG. 14A) extending through its full length and houses the deployable member 136 within that bore. The deployable member 136 is adapted to be retractably deployed in the bore 134 such that the distal end of the deployable member protrudes beyond the distal end of the internal bore 134. FIG. 14A and 14B show cross-sectional side and perspective views, respectively, of the distraction screw 10 in an assembled state.

Figure 16:
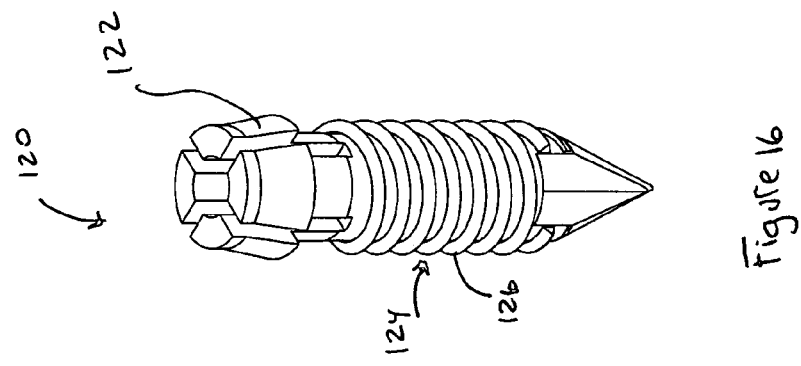
FIG. 16 shows a perspective view of the distal segment of the distraction screw.
Figure 15B:
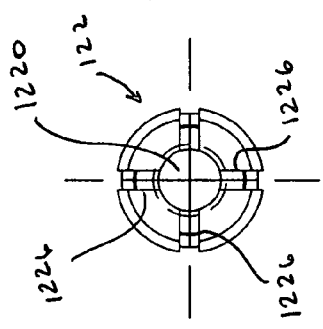
FIGS. 15A and 15B show side and top views of a distal segment of the distraction screw.
Figure 15A:
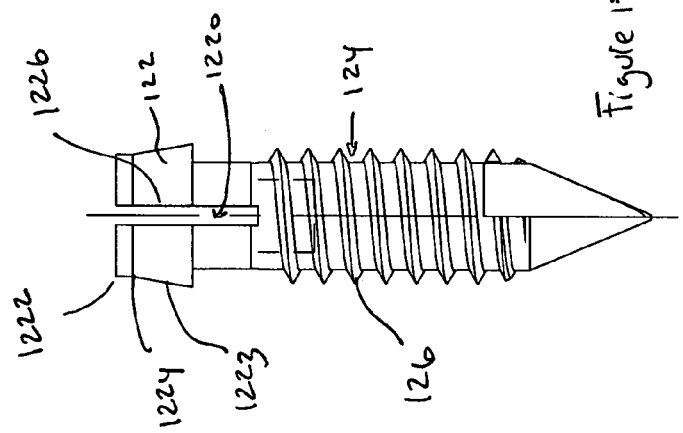

FIGS. 15A-B and 16 show various views of the distal segment 120 of the modular distraction screw 10. As mentioned, the distal segment 120 is comprised of a threaded shank portion 124 and a head portion 122. The shank portion 124 has threads 126, which can be self-tapping and/or self-drilling. Depending on the particular application, the shank 124 can be of variable lengths and diameter. Further, the threads can be of any design that is well known to be applicable for placement into mammalian bone.

The head 122 is circular with hollow central bore 1220. The upper aspect 1222 of the circular head is of uniform diameter but the lower portion 1223 of the head is of progressively greater diameter such that the head has a sloping sidewall below edge 1224. Threads are located within bore 1220 and are complementary to corresponding threads 128 (FIG. 13) of segment 136. The head 122 has slots 1226 intended to engage correspondingly-shaped projections 1322 (FIG. 17) of the distal aspect of the elongated body 132. The slots 1226 are preferably, but not necessarily, four in number and permit the head to collapse inward when centripetal force is applied to the outer wall of the head 122.

Figure 17:
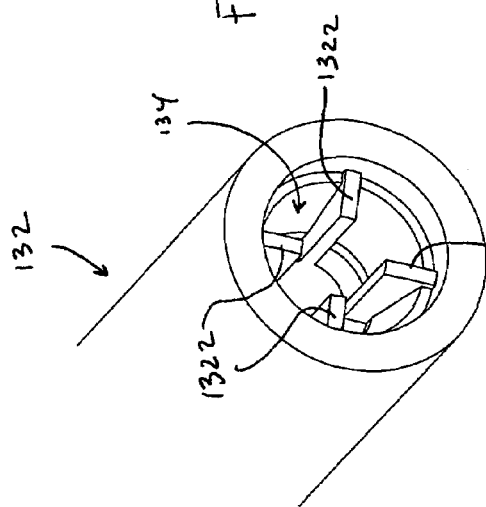
FIGS. 17 and 18 show enlarged, perspective and side views of a distal region of an elongated body of the distraction screw.
Figure 18:
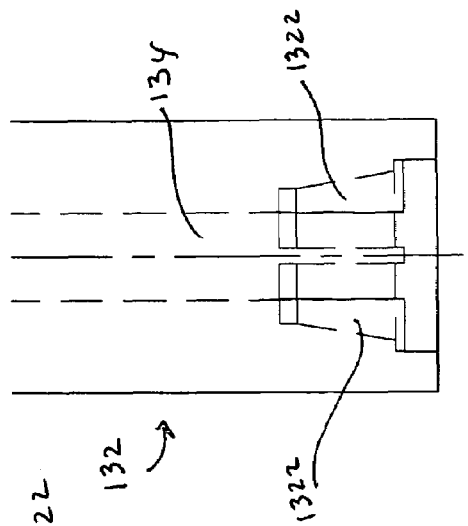

FIG. 17 shows a perspective view of a distal end of the elongated body 132, looking into the internal bore 134. FIG. 18 shows a side view of the distal end of the elongated body 132. One or more projections 1322 intended to engage slots 1226 of head 122 extend radially inward into the bore 134. As shown in FIG. 14A, the head 122 of the distal segment 120 is sized to fit within the distal region of the bore 134 such that the projections 1322 (FIG. 17) matingly engage the slots 1226 (FIG. 15B) in the distal segment 120. It should be appreciated that the mating engagement between the elongated body 132 and the distal segment 120 can vary in structure and configuration.

The deployable member 136 is advanced through bore 134 to engage distal segment 120 using the interaction of the complimentary threads 128 on the deployable member 136 and threads 1225 (FIG. 14B) within the bore 1220 of the distal member 120. The proximal head 1362 of the member 136 has a shape or structure that permits application of rotational force to member 136, which can be used to drive threads 128 and 1225 together and to lock members 132, 136 and distal segment 120 together. The proximal head 1362 is shown having a hex configuration that can be engaged by a wrench. However, while depicted as a hex configuration, any engageable configuration may be used to drive member 136.

The coupled proximal segment 130 and distal segment 120 employing the above-described means of engagement provide a modular distraction screw. When fully assembled, the screw will function as a unitary device. In a surgical application, a wrench (not shown) is attached to a tool attachment portion 179 (FIG. 14B) of the elongated body 132, and the distraction screw is positioned at a site of a bone. A rotational force is applied to the portion 179 of the elongated body 132 causing the entire distraction screw 10 to rotate in unison so that the threads 126 of the distal segment 120 engage the underlying bone and the shank 124 is advanced into the bone.

After the distraction screw is used to perform the bone work, the proximal segment 130 is detached from distal segment 120. The distraction screw is disassembled into its components by applying a rotational force to head 1362 of member 136 in a direction opposite (usually counter-clockwise) to that required for screw assembly (usually clockwise). The distal segment is held stationary while threads 128 and 1225 are disengaged by applying a counter force to distal segment 120 using the proximal portion 179 of the elongated body 132. In this way, the proximal segment is removed leaving the distal segment 120 attached to the vertebral bodies.

The distal segment provides enhanced structural integrity of the bone by reducing the stress concentration generally expected of an empty opening in a structural member. In addition, leaving the distal segment 120 attached to bone eliminates the robust bone bleeding encountered after removal of current, commercially-available distraction screws and obviates the need to fill the empty hole with a hemostatic agent.

The distal segment 120 will also help insure proper device placement. Since placement of the distraction screws is performed as the first step in the surgical procedure, the anatomical landmarks required to ensure proper alignment of the device in the desired anatomical plane are still intact.

Alternatively, a conventional one-piece distraction screw can be used to distract the vertebra during discectomy. After the bone work is finished, the conventional distraction screw is removed leaving an empty bone hole. An anchor similar to distal segment 120 is placed into the empty bone hole and guides the placement of the skeletal plate.

Placement Protocol

Figure 19:
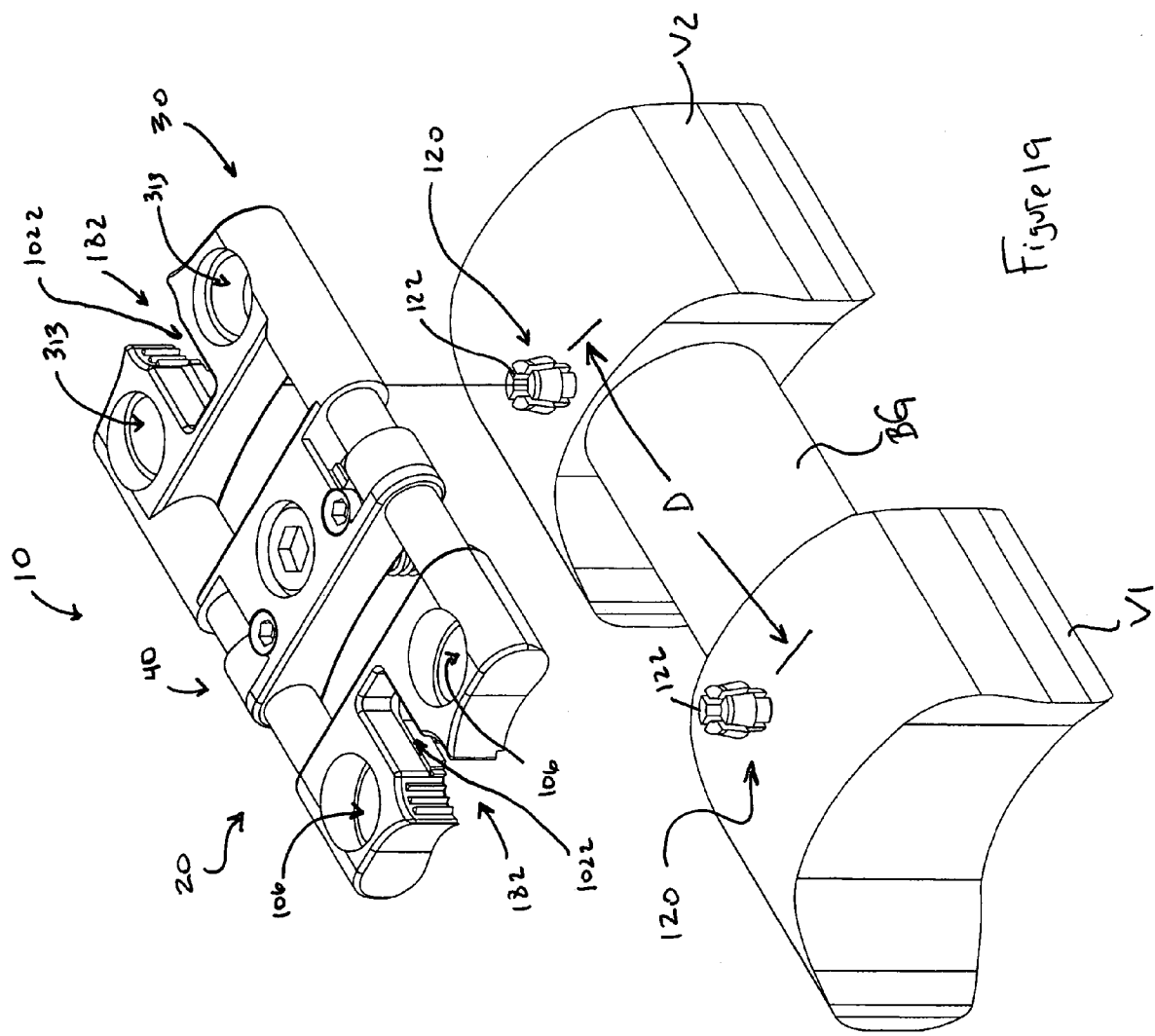
FIG. 19 shows the fixation device prior to mounting to a pair of vertebrae.

The removal of one or more vertebral bodies is accomplished by the step-wise removal of vertebrae until all pathological levels have been addressed. In an initial step of the procedure, the modular distraction screws 10 are placed into the vertebral bodies immediately above and immediately bellow the vertebra to be removed. For example, the screws 10 can be placed in vertebra V1 and V2. The modular distraction screws 10 are then used to distract the vertebra V1 and V2, open the intervening space between V1 and V2, and permit resection of the diseased segment(s) and placement of a bone graft into the evacuated space, as is known to those skilled in the art. After completion of the bone work, the proximal segment of each distraction screw 10 is removed leaving a distal segment 120 attached to each of the vertebral bodies V1 and V2 immediately above and below, as shown in FIG. 19. A graft BG is positioned between the vertebral bodies V1 and V2.

With the distal segments 120 of the distraction screws positioned in the vertebra V1 and V2, the assembled device 5 can be mounted to the vertebra V1 and V2. Advantageously, the distal segments 120 do not have to be removed and can be used as initial guideposts for guiding the device 5 onto the vertebra. FIG. 19 shows the assembled device 5 preparing to engage distal segments 120. The fastener screw shafts 106 and 313 in the components 20 and 30, respectively, are positioned and sized to receive bone screws that engage the underlying bony segment in the vertebra V1 and V2. The central channels 1022 in each component 20 and 30 is provided between the two fastener screw shafts 313 and 106. The central channels 1022 provide a space so that the device 5 can interact with the distal segments 120 of the modular distraction screws that have been left attached to vertebra V1 and V2. The device 5 is lowered onto the vertebra so that the distal segments 120 engage into the central channels 1022 and temporarily hold the device 5 against the vertebra. As shown in FIG. 1, the fastener screws 32 can then be inserted into the fastener screw shafts and attached to the bones to thereby fix the device 5 to the vertebra. FIG. 1 shows the device 5 attached to vertebral bodies V1 and V2 and the bone screws 32 in place.

The placement process is now described in more detail. With reference to FIG. 19, prior to placing the device onto the distal segments of the distraction screws 120, the distance D between the distal segments 120 attached to the vertebra V1 and V2 is measured and a fixation device 5 of appropriate length is selected based upon that measurement. The device 5 is delivered into the wound fully assembled and with screw 440 in the open position. That is, the components 20, 30 and 40 in an assembled state (as shown for example in FIG. 20A) with the screw 440 of component 40 in an open state. Advantageously, the person that is performing the placement process is not required to attach the components 20, 30 and 40 to one another during the placement process. As mentioned, the components 30 and 40 are fixed relative to one another when the screw 440 is in the open state and can travel across a predetermined distance relative to component 20. In this way, component 30 and 40 are fixed relative to each other but component 20 is freely movable and the device can accommodate a predefined range of sizes.

This is described in more detail with reference to FIG. 20A, which shows a top view of the device 5, including the components 20, 30, and 40, with the component 40 in an open state. When screw 440 is in the open state, components 30 and 40 are fixed relative to one another (because the head of screw 440 interlocks in the borehole 324 in component 30). Components 30 and 40 essentially function as a unitary piece 1111 that can travel across a range of motion comprised of a distance R1 relative to component 20. The unitary piece 1111 travels along an axis define by rods 210. The distance R1 is generally defined by the amount of space in the rod shafts 355 through which the rods 210 can move, as shown in FIG. 20A. The rods 210 can slide through the rod shafts up to a point where the tips of the rods abut an internal end of the rod shafts. When the screw 440 is in the open state, the overall length of the device 5 can be varied by moving components 30 and 40 relative to component 20.

With reference again to FIG. 19, after the length L of the device 5 is adjusted as described, the device 5 is snapped onto distal segments 120 at each end. The screw heads 122 can briefly collapse permitting the channels 1022 to slip below them. As each head springs back, the device is held between the screw heads 122 and the underlying bone of the respective vertebra. If the device 5 is poorly positioned because of bony irregularity, it can be removed to permit additional bone work. A removal instrument can be used to apply a centripetal force to the side walls of the head 122, causing the side walls to move inward, and permitting the fixation device to be removed. Alternatively, if the device is well positioned, fastener screw shafts 313 and 106 are moved into optimal position for bone screw placement. A screw driver is used to drive distal segment 120 further into the bone, thereby holding the fixation device stationary. The bone screws 32 are then easily placed through the fastener screw shafts into the underlying bone.

If compression is desired across the construct, it is applied by bringing component 20 and 30 closer together, such as by using a compression device. The compression is maintained until screws 440 are both tightened and closed. Once tightened, the compression device may be released and the force will be maintained by the fixation device.

As mentioned, with the screw 440 closed, components 20 and 40 are locked together (because the components 40 clamps around the rods 210) but both may move relative to component 30 within the confines of space 340. The device can accommodate bony subsidence for a distance allowed within space 340. This is described in more detail with reference again to FIG. 20B. With the screw of component 40 in the closed position, component 40 locks onto the rods 210 of component 20 such that components 20 and 40 essentially act as a unitary piece 1113. The piece 1113 comprised of the components 20 and 40 can move across a range of motion comprised of a distance R2 relative to component 30 with the range of distance R2 being defined by the amount of play in the space 340 in which the component 40 is positioned. The distance R2 is essentially equal to the difference between the length of the component 40 and the length of the space 340 in which component 40 is positioned. In one embodiment, the distance R2 is less than the distance R1. In another embodiment, R1 is less than R2, and in another embodiment, R2 and R1 are substantially equal. Thus, with the component 40 unlocked (corresponding to the screw 440 being open), the components 20 and 30 can move relative to one another across a distance R1 with the rods 210 guiding the movement. With the component 40 locked (corresponding to the screw 440 being closed), the components the components 20 and 30 can move relative to one another across a distance R2, which can differ from the distance R1. Thus, component 40 provides a convenient and efficient means of varying the amount of possible relative movement between components 20 and 30.

Extension of the fusion at a future date is easily accomplished without removal of the fixation device 5. Incorporation of the vertebral body immediately above or below into the fusion mass is started by placement of a modular distraction screw 10 into a vertebra (not shown) adjacent to the vertebra V1 or V2. A modified distraction screw 503 (shown in FIGS. 21A-21B) can then be coupled to the device 5 or to one of the vertebra V1 or V2 to which the device 5 is attached. Advantageously, the device 5 does not have to be removed from the vertebra V1 or V2 in order to install the distraction screw in that vertebra. This is because the components 20 and 30 each have a borehole 182 that can accommodate a distraction screw (such as the modified distraction screw 503) therethrough.

Figure 21A:
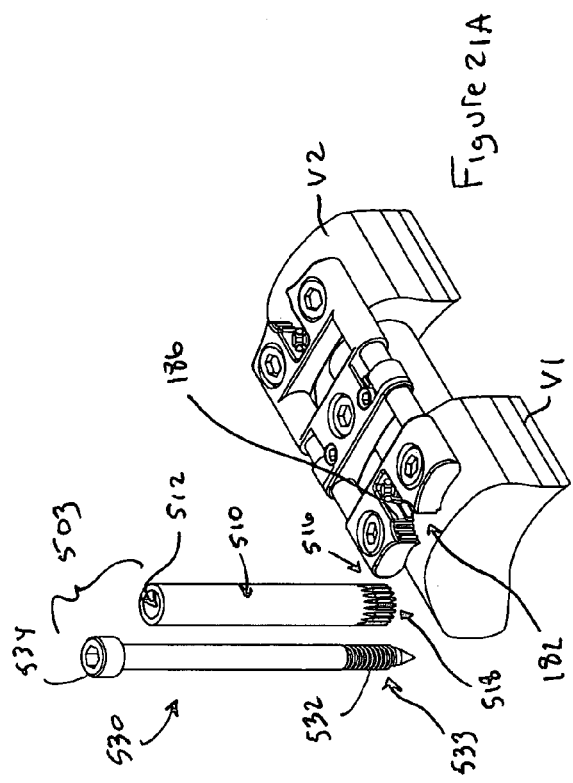
FIGS. 21A-21B show various views of a modified modular distraction screw in conjunction with a fixation device.
Figure 21B:
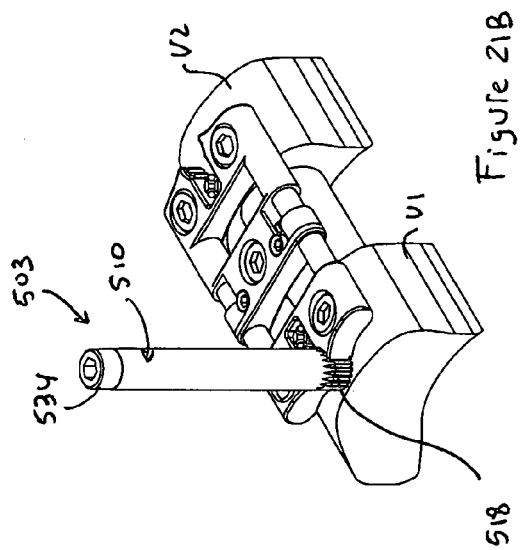

As shown in FIGS. 21A, the modified distraction screw 503 is used to engage the device 5 and/or the vertebra beneath borehole 182 of the fixation device 5 that is closest to the disc space to be removed. Vertebra V1 is used as an example in FIGS. 21A-21B. The components of that screw and its interaction with the device are illustrated in FIGS. 21A-21B. The modified distraction screw is formed by an elongated body 510 with an internal bore 512 (FIG. 21A) extending through its entire length to distal end portion 516. The internal bore 512 of the elongated body 510 is sized to receive and house an elongated deployable member 530, which is disposed within the internal bore 512. The deployable member 530 is adapted to be retractably deployed in the bore 512 such that a shanked distal end 533 extends beyond an opening 518 at the distal end of the internal bore 512. Threads 532 are located on the distal end 533 of the member 530 and a head 534 is disposed on the other end. The head 534 has a diameter greater than that of the internal diameter of bore 512. A depression 536 is formed within head 534 so as to permit engagement and rotation of the deployable member 530 with a complimentary driver. While depicted as a hexagonal depression intended to receive an Allen's wrench, any alternative means and arrangements for engaging and rotating the deployable member 530 can be employed.

Adjacent to the distal end 516 of elongated body 510, spines 518 are placed which are designed to compliment and engage the spines 186 in the sidewall of the borehole 182. The spines on elongated body 510 are used to engage the end coupler immediately adjacent to the disc space to be fused thereby providing an engagement between the distraction screw 503 and the device 5. The threads 532 on the distal end of the deployable member 530 are used to engage the bone surface at the bottom of borehole 182, thus firmly affixing the modified distraction screw 503 to the bone V1. The modified distraction screw 503 and the modular distraction screw previously affixed to the adjacent vertebra are used to distract the vertebral bodies, permitting work on the intervening disc space. When the discectomy and subsequent bone work are finished, the modular distraction screw previously affixed to the adjacent vertebra is separated leaving a distal segment 120 attached to the adjacent vertebra as described above. The modified distraction screw 503 is then removed from the borehole 182, leaving a bare borehole 182, as shown in FIG. 22. A modular device 2202 having an end coupler 2203 can be modularly attached to the device 5 by mating the end coupler 2203 with the borehole 182. The end coupler 2203 has a size and shape that can mate with the borehole 182, such as spines that matingly correspond to the spines in the borehole 182. FIG. 23 shows the end coupler 2203 of the modular device 2202 coupled with the borehole 182. The modular device 2202 is shown only partially in FIGS. 22 and 23, which indicates that the modular device could comprise any of a wide variety of devices. In one embodiment, the modular device 2202 comprises a separate fixation device 5 used to span the distance between the distal segment in the adjacent vertebra and the borehole 182. In this way, the fusion is readily extended to an adjacent level without removal of the original fixation device.

Alternately, extension of the fusion can be performed without the use of the modified screw 503 described above. For example, a conventional one-piece distraction screw (without spines) can be used to engage the underlying bone alone through the borehole 182. A modular distraction screw is placed in the vertebral body adjacent to the disc space to be fused. These two distraction screws are used to distract the vertebral bodies, permitting work on the intervening disc space. The remainder of the fusion extension is then performed as described above.

Figure 24A:
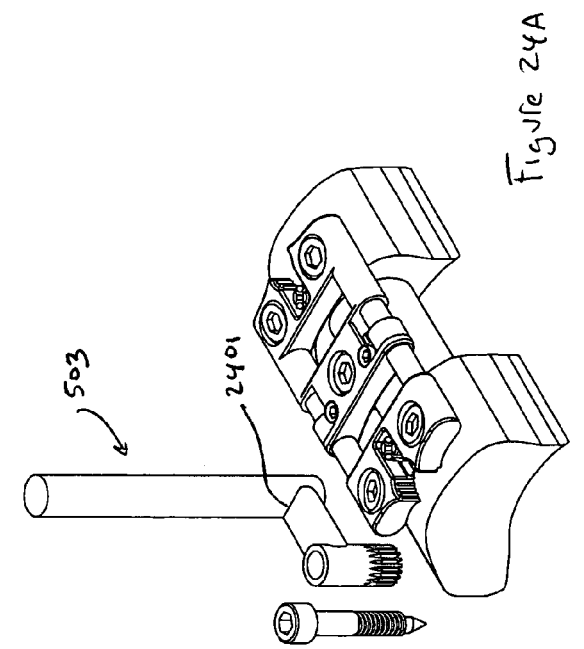
FIGS. 24A-24B show various views of an offset distraction screw in conjunction with a fixation device.
Figure 24B:
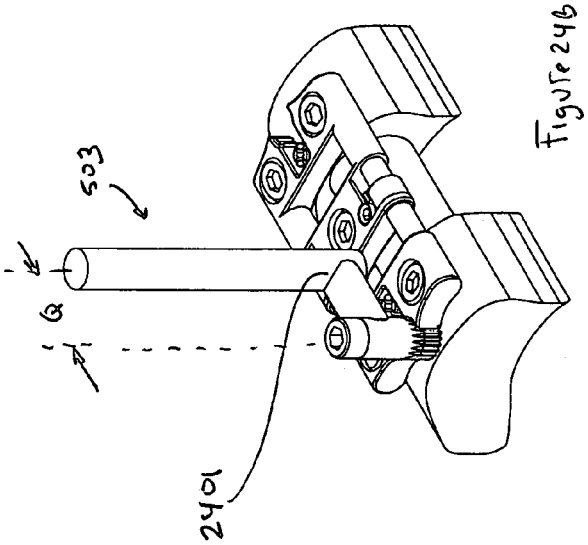

Occasionally, a portion of the fixation device 5 abuts the disc space adjacent the vertebra such that placement of the modified distraction 503 screw into the borehole 182 hinders surgical access to the disc space. FIGS. 24A-24B shows an offset modified distraction screw 503 which may be used in this setting and illustrates its placement. The screw components are similar to those described above for the non-offset screw. The offset modified distraction screw 503 includes a bend 2401 that offsets a proximal region of the screw 503 a distance Q from a distal region of the screw.

The present invention provides a convenient, easily placed, variable length rod-based bone fixation that is capable of accommodating bony subsidence at the level of the subsiding bone. The device also has a modular design that permits extension of the fusion at a future date.

Alternative Designs

In the previously-described embodiments, the central channels 1022 opened into the boreholes 182. Since the head 122 of the distal segment 120 of the modular distraction screw 10 can be introduced onto the superior aspect of each central channel through the end opening of the borehole 182, the head 122 need not be collapsible. Thus, as an alternative design, the head 122 can be made solid (not shown).

Figure 25:
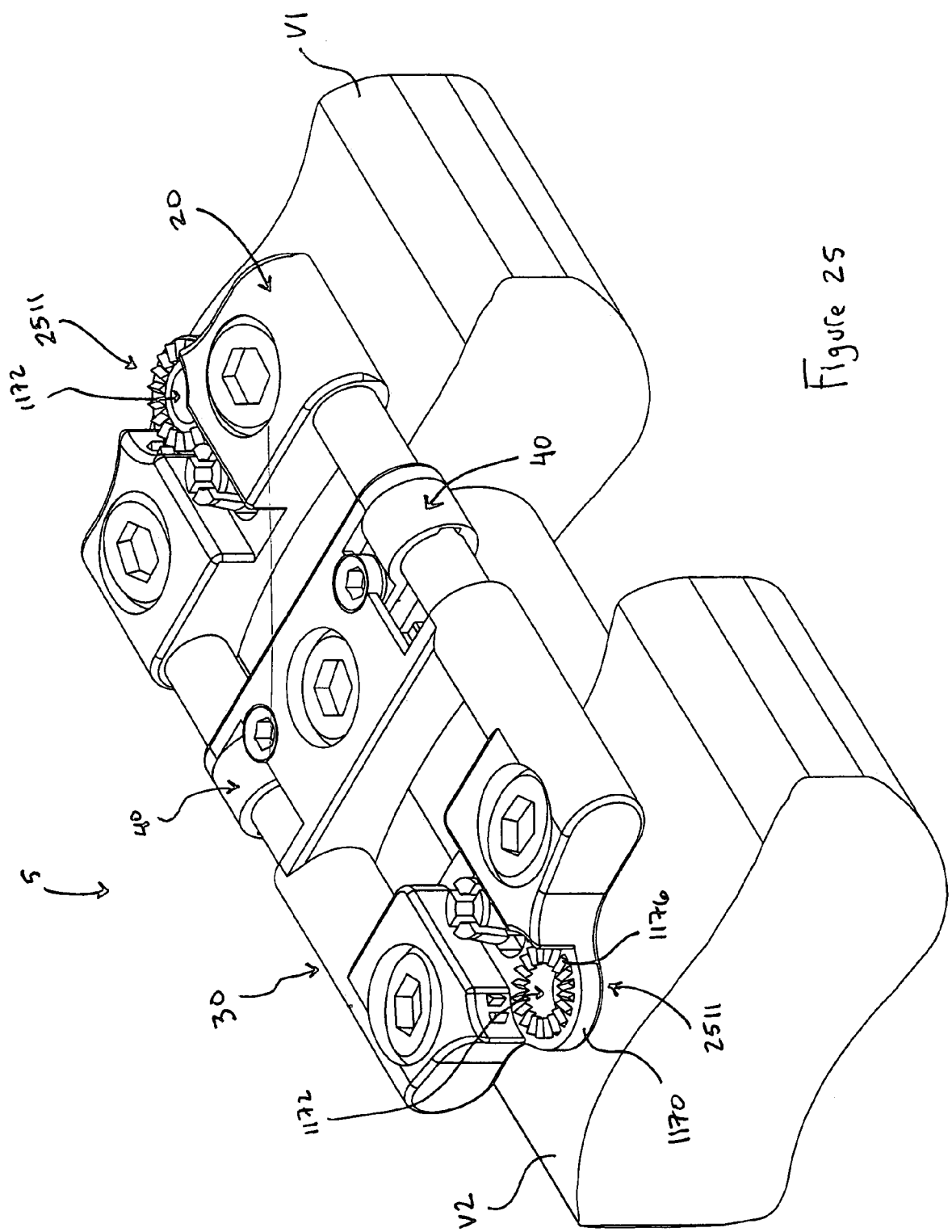
FIG. 25 shows a second embodiment of the fixation device.

A second embodiment of the device 5 is illustrated in FIG. 25. In this design, a partial thickness end coupler 2511 is located at each end of the fixation device. A projection 1170 is formed by the end coupler and can optionally be placed in the midline of the device 5. The projection 1170 has a central hole 1172 which contains threads. Engagement structures such as spines 1176 may be placed along the top of the projection 1170 to mate with the complimentary spines of the add-on modular attachments. While depicted as triangular, the spines may be projections of any geometric configuration, and may occupy any part of the region of the end coupler 2511. Alternatively, these surfaces may be textured or left smooth.

Figure 26:
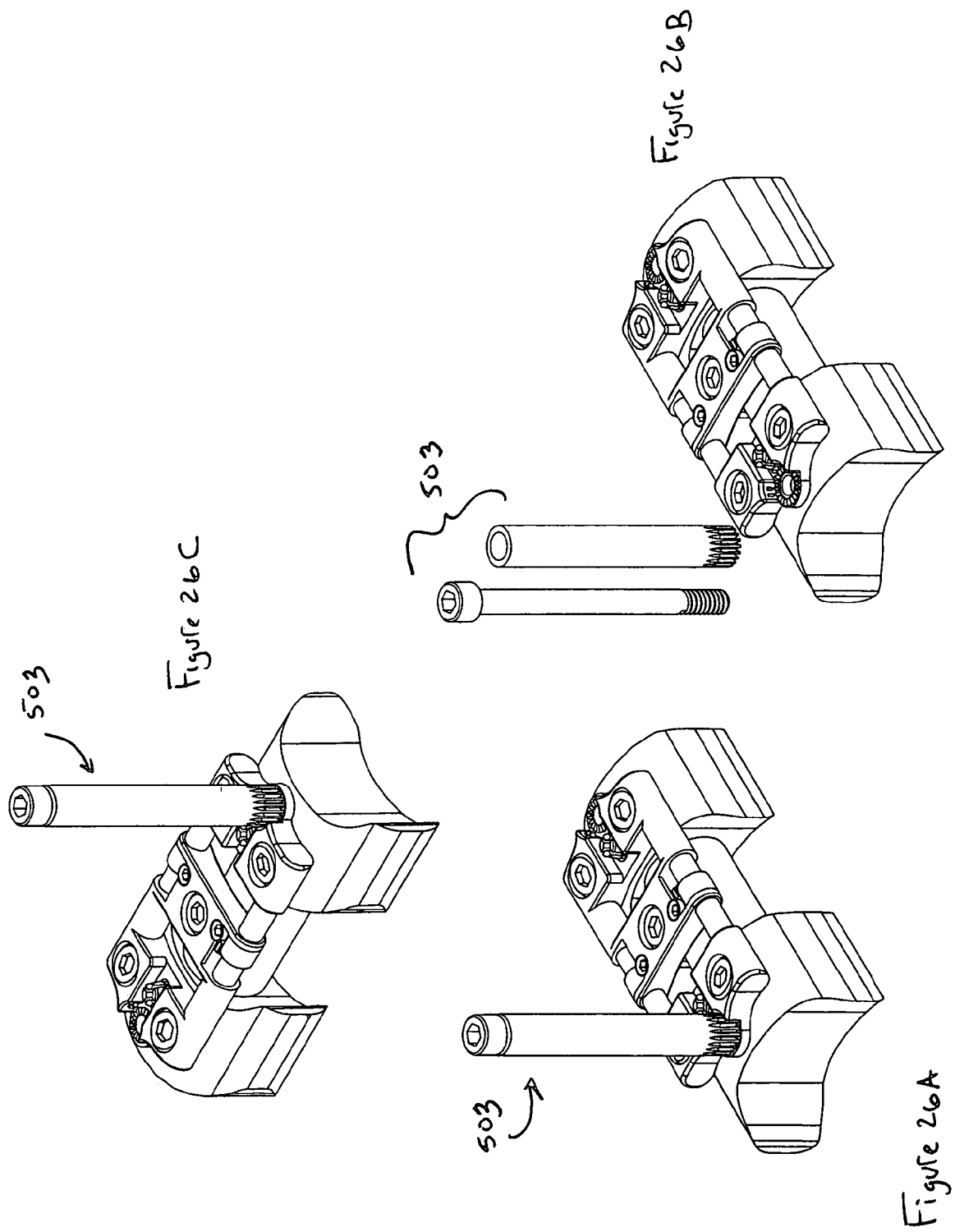
FIGS. 26A-26C shows a second embodiment of a modular distraction screw for use with the second embodiment of the fixation device.

Using the end-coupler 2511, the fusion can be extended at a future date in the same manner as discussed above. This procedure is started by placement of modular distraction screw 10 into the adjacent vertebra. A modified distraction screw is used to engage the end-coupler 2511 of the existing fixation device. The modified distraction screw can be similarly configured as the screw 503 described above with the distal end of the screw modified to mate with the end coupler 2511, such as is shown in FIGS. 26A-26C. The components of the modified distraction screw 503 and the assembled screw 503 are illustrated in FIGS. 26A-26C. As mentioned, the screw is similar to that discussed above. However, the threads at the distal end of the deployable member are designed to engage threads inside the hole 1172 of the end-coupler 2511 and/or engage the underlying bone. The modified distraction screw and the modular distraction screw previously affixed to the adjacent vertebra are used to distract the vertebral bodies, permitting work on the intervening disc space. When the discectomy and subsequent bone work are finished, the modular distraction screw is separated leaving a distal segment 120 attached to vertebral body, as described above. The modified distraction screw is removed leaving a bare end-coupler. A separate fixation device is used to span the distance between the distal segment and the end coupler. In this way, the fusion is readily extended to an adjacent level. The screw can be modified to have an offset configuration, such as was described above with reference to FIGS. 24A-24B.

Figure 27:
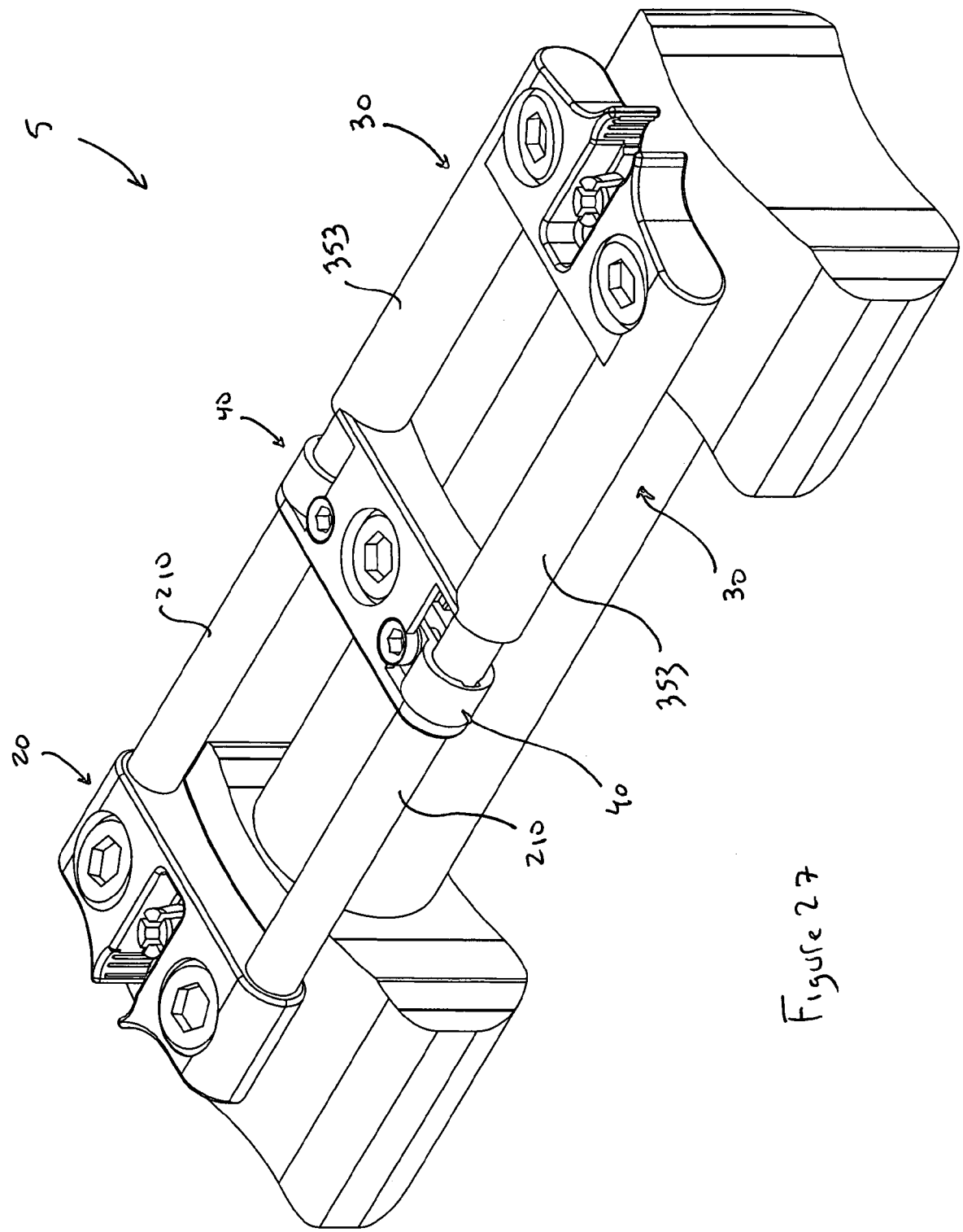
FIGS. 27 and 28 show perspective views of additional embodiments of the fixation device.
Figure 28:
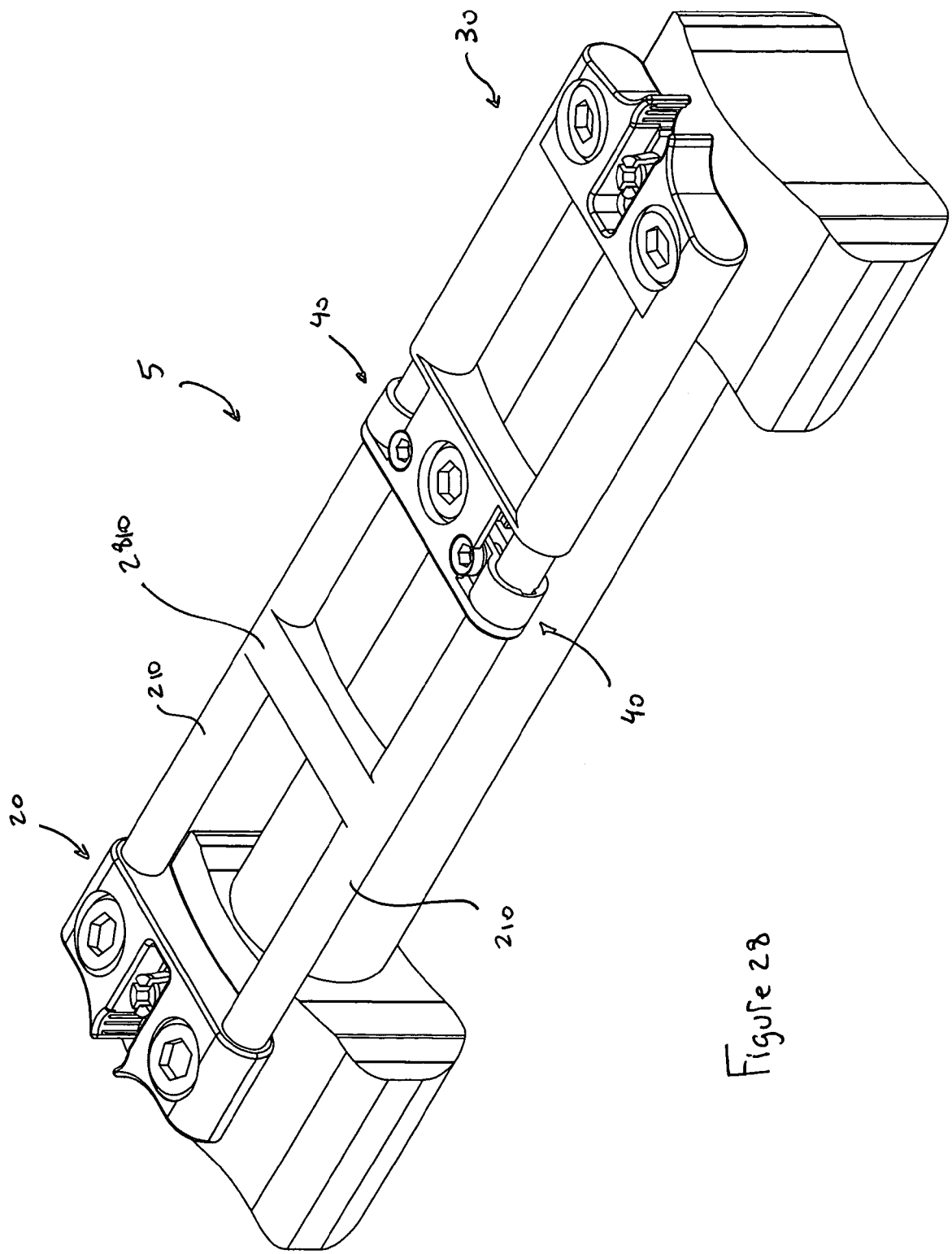

FIG. 27 shows another embodiment of the fixation device 5 wherein the device has a length that is longer than the device 5 described above. The rods 210 have an elongated configuration such that the fixation device 5 covers a larger distance than the previously-described device. The side regions 353 of the component 30 have lengths that are configured to accommodate the lengths of the rods 210. FIG. 28 shows yet another embodiment, wherein a support structure 2810 is interposed between the rods 210 to provide structural support to the rods 210. The support structure 2810 helps to maintain the integrity of the spacing between the rods 210 and reduces the likelihood the rods 210 moving apart or toward one another.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A bone fixation device for retaining vertebra of a spinal column in a desired spatial relationship, comprising:
    a first member connectable to a first vertebra;
    a second member connectable to a second vertebra and interconnected with the first member, wherein the first and second members are movable relative to one another across a range of motion;
    at least one elongate rod interconnecting the first member to the second member;
    an adjustor member that transitions between a first state wherein the adjustor member is fixed relative to the first member and movable relative to the second member, and a second state wherein the adjustor member is fixed relative to the second member and movable relative to the first member, wherein the range of motion between the first member and second member spans a first, limited distance when the adjustor member is in the first state, and wherein the range of motion between the first member and second member spans a second, limited distance when the adjustor member is in the second state.

2. A device as in claim 1, wherein the first distance is not equal to the second distance.

3. A device as in claim 1, further comprising at least one elongate rod interconnecting the first member and the second member.

4. A device as in claim 1, wherein the range of motion is linear.

5. A device as in claim 1, wherein the first member includes a distraction screw coupler that permits the first member or the first vertebra to be coupled to a distraction screw while the first member is connected to the first vertebra.

6. A device as in claim 5, wherein the distraction screw coupler comprises a borehole or slot sized to receive therethrough a distraction screw.

7. A device as in claim 6, wherein at least a portion of the borehole or slot can mate with a portion of the distraction screw.

8. A device as in claim 1, wherein the first member includes a modular coupler that can mate with a second bone fixation device.

9. A device as in claim 1, wherein the range of motion is curved.

10. A bone fixation device for retaining vertebra of a spinal column in a desired spatial relationship, comprising:
    a first member connectable to a first vertebra;
    a second member connectable to a second vertebra and interconnected with the first member, the first and second members being movable relative to one another;
    at least one elongate rod interconnecting the first member to the second member;
    an adjustor member that can be adjusted to vary the degree of movement of the first member relative to the second member, wherein the adjustor member adjusts between a first state wherein the adjustor member is fixed relative to the first member and movable relative to the second member, and a second state wherein the adjustor member is fixed relative to the second member and movable relative to the first member, wherein the degree of movement spans a first range when the adjustor member is in the first state and wherein the degree of movement spans a second range when the adjustor member is in the second state.

11. A bone fixation device for retaining vertebra of a spinal column in a desired spatial relationship, comprising:
    a first member connectable to a first vertebra;
    a second member connectable to a second vertebra and interconnected with the first member, the first and second members being movable relative to one another;
    at least one elongate rod interconnecting the first member to the second member;
    means for adjusting the range of motion of the first member relative to the second member, wherein the range of motion spans a first distance or a second distance and wherein the means for adjusting is adapted to transition between a first state wherein the means for adjusting is fixed relative to the first member and movable relative to the second member, and a second state wherein the means for adjusting is fixed relative to the second member and movable relative to the first member.

* * * * *